US007103188B1

(12) United States Patent
Jones

(10) Patent No.: US 7,103,188 B1
(45) Date of Patent: Sep. 5, 2006

(54) VARIABLE GAIN ACTIVE NOISE CANCELLING SYSTEM WITH IMPROVED RESIDUAL NOISE SENSING

(76) Inventor: Owen Jones, 12 The Chequers, Alreford Colchester (GB) CO7 8BW (*) Notice: Subject to any disclaimer, the term of this patent is extended or adjusted under 35 U.S.C. 154(b) by 0 days.

(21) Appl. No.: 09/595,558

(22) Filed: Mar. 8, 1999

Related U.S. Application Data

(63) Continuation of application No. 08/968,873, filed on Nov. 5, 1997, now Pat. No. 6,118,878, which is a continuation of application No. 08/082,402, filed on Jun. 23, 1993, now abandoned.

(51) Int. Cl.
*A61F 11/06* (2006.01)
*G10K 11/16* (2006.01)
*H03B 29/00* (2006.01)

(52) U.S. Cl. ................. 381/71.9; 381/71.13; 381/71.2; 381/72

(58) Field of Classification Search .................. 381/87, 381/71.1, 71.2, 71.6, 71.8, 71.9, 71.13, 71.14, 381/72, 73.1, FOR. 123
See application file for complete search history.

(56) References Cited

U.S. PATENT DOCUMENTS

| | | | | |
|---|---|---|---|---|
| 4,654,871 | A | 3/1987 | Chaplin et al. | 381/72 |
| 4,677,677 | A | 6/1987 | Eriksson | 381/71 |
| 4,742,887 | A | 5/1988 | Yamagishi | 181/129 |
| 4,833,719 | A | 5/1989 | Carme et al. | 381/72 |
| 4,953,217 | A | 8/1990 | Twiney et al. | 381/72 |
| 4,985,925 | A | 1/1991 | Langberg et al. | 381/72 |
| 5,018,202 | A | 5/1991 | Takahashi et al. | 381/71 |
| 5,091,954 | A | 2/1992 | Sasaki et al. | 381/72 |
| 5,111,506 | A | 5/1992 | Charpentier et al. | 381/68.4 |
| 5,134,659 | A | 7/1992 | Moseley | 381/72 |
| 5,138,664 | A | 8/1992 | Kimura et al. | 381/72 |

(Continued)

FOREIGN PATENT DOCUMENTS

EP 212640 B1 10/1991

(Continued)

*Primary Examiner*—Xu Mei

(57) ABSTRACT

An active noise cancellation system includes a series of features for more effective cancellation, greater reliability, and improved stability. A particular feature adapted for headset systems includes locating a residual microphone radially offset from the center of a sound generator to detect a signal more similar to that incident upon the eardrum of the user. In addition, an open back headset design includes perforations on the side of the headset instead of the back, so that the perforations are less susceptible to inadvertent blockage. The system also includes a mechanism for detecting changes in the acoustic characteristics of the environment that may be caused, for example, by pressure exerted upon the earpieces, and that may destabilize the cancellation system. The system automatically responds to such changes, for example, by reducing the gain or the frequency response of the system to preserve stability. The system further includes other methods for detecting imminent instability and compensating, such as detecting the onset of signals within enhancement frequencies characteristic of the onset of instability, and adjusting the gain or frequency response of the system or suppressing the enhanced signals. The system further includes a mechanism for conserving battery life by turning the system off when sound levels are low, or adjusting the power supply to the system to correspond to the current power requirements of the system.

3 Claims, 25 Drawing Sheets

U.S. PATENT DOCUMENTS

| | | | | |
|---|---|---|---|---|
| 5,144,678 | A | 9/1992 | Lenz | 381/183 |
| 5,172,416 | A * | 12/1992 | Allie et al. | |
| 5,182,774 | A | 1/1993 | Bourk | 381/71 |
| 5,251,263 | A | 10/1993 | Andrea et al. | 381/71 |
| 5,259,033 | A | 11/1993 | Goodings et al. | 381/68 |
| 5,276,740 | A | 1/1994 | Inanaga et al. | 381/187 |
| 5,327,507 | A | 7/1994 | Suzuki | 381/183 |
| 5,425,105 | A * | 6/1995 | Lo et al. | |
| 5,481,615 | A | 1/1996 | Eatwell et al. | 381/71 |
| 5,535,283 | A * | 7/1996 | Saruta et al. | |

FOREIGN PATENT DOCUMENTS

| | | |
|---|---|---|
| GB | 2172470 | 1/1989 |
| GB | 2265790 | 10/1993 |
| GB | 2160070 A | 12/1995 |

* cited by examiner

VARIABLE GAIN ACTIVE NOISE CANCELLING SYSTEM WITH IMPROVED RESIDUAL NOISE SENSING

This application is a continuation, of application Ser. No. 08/968,873, filed Nov. 5, 1997, now U.S. Pat. No. 6,118,878, which is continuation of application No. 08/082,402, filed Jun. 23, 1993 now abandoned (application status etc.), which is hereby incorporated by reference.

BACKGROUND OF THE INVENTION

1. Field of the Invention

The present invention relates to active noise cancellation systems, and more particularly, to headsets utilizing active noise cancellation.

2. Description of the Related Art

Conventionally, passive headsets and over-the-ear earplugs comprise a pair of earpieces coupled by a resilient headband. An annular foam pad attached to each earpiece forms a cushion between the shell of the earpiece and the user's head. The resilient headband presses the earpieces against the user's head. Ambient sound is attenuated before it reaches the wearer's ear by occlusion of sound by the earpieces and absorption of transmitted sound by materials within the earpieces. The degree of attenuation achieved depends upon the nature of the ambient noise and the qualities and characteristics of the individual headset or earplugs.

In various applications, however, passive attenuation is insufficient. Some environments are simply too noisy for comfort or even safety with only passive earplugs. In other environments, the elimination of extraneous noise is paramount, and satisfactory results cannot be achieved using passive means. Although the amplitude of the extraneous noise may be significantly diminished, it is almost impossible to completely isolate the wearer from extraneous noise using passive means. In addition, passive earplugs attenuate all sound, regardless of whether the wearer needs or wants to hear particular sounds.

Active noise cancellation systems eliminate unwanted sound using destructive interference. Cancellation is achieved by propagating anti-noise, identical to the unwanted soundwaves but inverted, which interacts with the unwanted waveform and results in cancellation. A feedback active cancellation headset typically includes a sound generator in each earpiece for producing anti-noise, and a residual microphone, also located in each earpiece, to provide feedback signals to a controller which generates the proper anti-noise signals. Each microphone detects the unwanted noise within each earpiece and provides corresponding signals to the controller. The controller supplies anti-noise signals to the sound generator corresponding to the noise detected in the earpieces, but inverted, with respect to the unwanted waveform. When the anti-noise interacts with the noise within each earpiece, destructive interference between the noise and the anti-noise cancels the unwanted sound.

Ideally, the residual microphone in feedback systems perceives the same sounds as the eardrum of the listener. In this regard, effective proximity to the eardrum is vital; the goal of the cancellation systems is to reduce the unwanted noise at the eardrum to zero, but in fact operates upon the noise detected by the microphone. Consequently, it is desirable that the microphone be placed sufficiently close to the eardrum to detect a reasonably similar noise field to that perceived by the listener. The eardrum, however, is located deep within the ear canal. Placing a microphone within the ear canal is generally impractical and very uncomfortable for the user. In addition, locating the microphone a significant distance away from the sound generator introduces a phase shift between the residual and cancellation signals and causes instability. As a result, active cancellation systems conventionally approximate the sound perceived by the listener by locating the microphone as close to the ear canal as possible without actually penetrating it.

Conventionally, the microphone is placed directly between the sound generator and the ear in axial alignment with the sound generator, and hence the anti-noise field, e.g. disposed at the center of a grille covering the sound generator. For headsets that do not form an acoustic seal between the earpiece and the user's head, the cancellation sound detected such a center-disposed microphone is significantly different from the cancellation sound perceived by the user. Because of the proximity of the microphone to the sound generator and center of the anti-noise field, the cancellation sound detected by the microphone is attenuated very little. As the point of measurement moves away from the sound generator, the level of detected sound decreases due to the relatively low acoustic resistance of the foam cushion between the earpiece shell and the user's head. Thus, the cancellation sound incident upon the user's eardrum is of a significantly lower amplitude than the primary sound detected by the microphone. Consequently, the effectiveness of the cancellation system suffers because the anti-noise in the ear canal is insufficient to cancel the soundwaves.

To enhance the low frequency response, some headphones use an open back design. For example, in many designs, a series of perforations are formed in the back of the headset, allowing air to move in and out of the chamber behind the sound generator to enhance lower frequency response. While the headphones are in use, however, the perforations may be covered or obstructed, for example by the user's hands, or by a pillow on an airplane. When the perforations are obstructed, the low frequency sensitivity of the headphones drops. In addition, obstruction of the perforations changes the frequency response of feedforward systems in midband frequencies that are within crucial cancellation frequency ranges.

Another problem associated with feedback cancellation systems is that they are prone to instability. Feedback systems tend to become unstable, for example, if the bandwidth of the system is too broad or the gain of the system is too high. When instability occurs, the system usually emits a loud noise that is generally unpleasant and occasionally dangerous. Consequently, the maximum range and effectiveness of feedback systems are limited by parameters designed to keep the feedback system stable.

To effect maximum cancellation, the waveform of the interacting anti-noise should exactly match the unwanted waveform, but should be inverted. The acoustic properties of each earpiece, however, affect the characteristics of the anti-noise waveform. The effect of the acoustic properties may be corrected by processing the residual signal according to a transfer function characteristic of the acoustic properties of the system to compensate for the effects. However, these acoustic properties of the headset are not constant under all conditions, and may vary with the force applied to the earpiece onto the user's head. When high pressure is applied to the earpiece, or when the headset is removed from the user's head, the variation of the earpiece's acoustic properties, particularly the volume and acoustic resistance, may cause instability in the feedback loop. This instability, in turn, causes the control loop to generate unstable oscillations, producing unpleasant and potentially even harmful noise.

In contrast to feedback systems, some active noise cancellation systems use feedforward techniques. In a feedforward system, an external microphone is placed in a noise field between the listener and the noise source. As the soundwaves propagate toward the listener, the microphone detects the noise before it reaches the listener's ears. The microphone provides a signal to a controller that generates a cancellation signal according to the detected noise. The cancellation signal is provided to a sound generator which generates anti-noise near the listener's ear to effect cancellation. Because the propagation speed of the soundwaves and the distance between the listener's ear and the external microphone are known, the controller precisely times the generation of the cancellation signal so that the proper phase relationship with the undesired sound is maintained and adjusts the amplitude to provide the correct cancellation level. Like feedback systems, application of abnormal force to an earpiece using a feedforward cancellation system disrupts the operation of the active noise cancellation system. Instead of causing instability, however, changes in the acoustic properties reduce the effectiveness of the cancellation system.

In at least one system, as disclosed in PCT Application PCT/US91/06636, filed Sep. 13, 1991, by Todter, et al., a feedforward system is purported to be combined with a feedback system to provide added cancellation. The feedforward signal is mixed with the cancellation signal generated by the cancellation circuitry and applied as a drive signal to the sound generator. However, the feedforward signal, when mixed with the cancellation signal to drive the sound generator, is in conflict with the feedback operation of the circuit, i.e. the feedforward signal is itself subject to cancellation. Consequently, although the feedforward system may add to the cancellation to some extent, its effectiveness is reduced due to cancellation of the feedforward signal by the feedback system.

The voltage level supplied to the system's power amplifier tends to affect the level of amplification, but also affects power consumption. In many applications, active noise canceling headsets employ batteries to supply power to the controller, the sound generating unit, and microphones. Use of batteries avoids the necessity of a power cable connecting the headset to a power source. A power cable tends to reduce the mobility of the headset wearer and presents a hazard to others in the area. Batteries, on the other hand, have only a limited operational lifespan before needing replacement or recharging. Frequent replacement or recharging of the batteries costs money and time, and imposes an inconvenience on the user.

In addition, many noise cancellation headsets are designed not only to cancel unwanted noise, but to provide particular sounds to the user. For example, headphones for listening to music or for use by pilots ideally cancel extraneous noise, and transmit particular desired sounds to the listener. Conventionally, the desired input signal is mixed with the residual signal from the internal microphone so that the desired signal is not canceled by the system. Feedback noise cancellation systems, however, because of their limited bandwidth, exhibit a high frequency rolloff having a relatively low cutoff frequency. Because of this cutoff frequency, higher frequencies of the desired sound tend to be attenuated, degrading the quality of the signal. Consequently, an equalizer must be added to return the sound to its proper amplitude.

SUMMARY OF THE INVENTION

A headset according to the present invention provides an improved active noise cancellation headset. In accordance with the various aspects of the present invention, the headset: is less susceptible to instability; conserves power and thus extends battery life; provides for improved cancellation at the user's ear; is less susceptible to variation in low frequency response; provides for more accurate reproduction of desired sounds input to the noise cancellation system; and provides an open back with perforations less susceptible to blockage. The headset system suitably includes an earpiece, a mechanism to hold the earpiece against the user's head, and an active noise cancellation circuit. The noise cancellation circuit cooperates in a feedback loop or a feedforward system, including a microphone and sound generator in the earpiece.

According to one aspect of the present invention, an active noise cancellation headset system provides cancellation of sound approximating the sound at the user's eardrum. Instead of positioning the microphone to detect the maximum amplitude of the cancellation signal generated by the sound generator, the microphone is disposed to detect an attenuated level of sound that more closely resembles the sound actually incident upon the eardrum and perceived by the listener. For example, the microphone may be disposed radially off-center from the sound generator.

Variations in low frequency due to obstruction of the perforations on the back of open back headsets is addressed by another aspect of the present invention. Perforations are disposed on the side of the headset to lessen the likelihood that the perforations are inadvertently obstructed by the user. Consequently, the transfer function of the cancellation system remains constant and the cancellation system retains its effectiveness across its bandwidth.

According to another aspect of the present invention, system stability is improved. It has been determined that as the feedback system approaches instability, high frequency signals in a predetermined frequency range (referred to herein as the high frequency enhancement region) are enhanced instead of canceled. Similarly, low frequency signals within a predetermined low frequency enhancement region are also enhanced as the system approaches instability. Impending instability is detected by monitoring the ratio of the external noise amplitude to the internal noise amplitude in either or both of the enhancement frequency regions. Soundwaves within the monitored enhancement frequency range are detected by the internal microphone and by a microphone external to the earpiece. If the ratio of the signals exceeds a stability threshold, the cancellation system is approaching instability. In response, the gain of the noise cancellation system is reduced to maintain stability.

Alternatively, the midband range of the residual signal may be monitored to determine whether the cancellation signal exceeds a threshold at which instability occurs. If so, the gain is reduced to maintain stability.

According to another aspect of the present invention, a headset system may also include a mechanism for attenuating signals in the enhancement region. A feedforward system having a microphone positioned between the noise source and the sound generator is employed. The feedforward system is designed to cancel high frequencies, but have little effect on low and midband frequencies. The frequencies canceled include those in the enhancement region, thus reducing the amplitude of sound in the enhancement frequency range and improving the overall quality of the cancellation system. Alternatively, the feedforward system may be designed to cancel frequencies within the cancellation band and incorporated into the feedback system to add to the effectiveness of the cancellation system. The feedforward signal is applied as an input to the cancellation circuit (as opposed to a drive signal to the sound generator) to avoid counteraction between the feedforward and feedback portions of the system. As a result, the cancellation system provides sufficient cancellation with reduced feedback loop gain, providing added stability.

According to another aspect of the present invention, it is recognized that potential instability may be caused by pressure variations on the earpiece. The system produces a pressure signal corresponding to the pressure of the earpiece against the user's head. The cancellation system gain and the coefficients for low frequency filters in the system are varied accordingly to reduce the low frequency response and maintain stability. To this end, in accordance with yet another aspect of the invention, a suitable arrangement of switches and transducers may be employed to avoid the instability due to an earpiece being pressed against the user's head and the instability due to the headset being removed from the user's head.

Instability may also be sensed by introducing a subsonic acoustic signal into the earpiece, detecting the subsonic acoustic signal, and producing the pressure signal in response to the amplitude of the detected subsonic acoustic signal. The subsonic acoustic signal may be introduced into the earpiece by applying the output of a subsonic signal generator to the sound generating unit within the earpiece. The microphone, in series with a low pass or bandpass filter, detects the subsonic acoustic signal within the earpiece. By measuring changes in the detected subsonic signal, the amount of pressure and likelihood of instability may be established.

In accordance with yet another aspect of the present invention, it has been found that when an earpiece is pressed against the head of a user with abnormal force, the feedback loop becomes unstable and begins to oscillate. The resultant oscillations comprise a low frequency drone and a high frequency squeal. The squeal is at a high sound pressure level and causes discomfort to the user. Accordingly, excess pressure between the earpiece and the user's head may be detected by identifying the onset of the drone and/or squeal. Where it is acceptable for the gain of the feedback loop to be reduced to zero, the feedback loop may be broken, for instance by isolating the sound generating unit, or the power supply to the controller may be interrupted.

In another aspect of the present invention, the active noise cancellation system includes a mechanism for extending battery life. According to one aspect of the present invention, power consumption is controlled in accordance with the amplitude of the noise to be canceled. This may be implemented by employing a switch or transducer responsive to a control signal indicative of the amplitude of the noise to be canceled to cut or vary the supply voltage according to the current needs of the system; when the control signal indicates a noise level below a predetermined threshold, the power supply to part of the system is interrupted or reduced, thus conserving power and battery life.

In accordance with another aspect of the invention, a switch mode voltage regulator regulates and supplies power to a portion of the system. The regulator, responsive to the control signal representative of the amplitude of the noise to be canceled, reduces the voltage applied to the cancellation system as the amplitude of the noise to be canceled decreases, and increases the voltage applied to the portion of the system as the amplitude of the noise to be canceled increases. Alternatively, an amplifier biasing circuit responsive to the control signal may vary the bias of an amplifier for the anti-noise as a function of noise amplitude.

According to another aspect of the present invention, a desired input signal is provided to the system by mixing the input signal with the residual signal generated by the microphone and also mixing the input signal with the cancellation signal provided to the sound generator. High frequency components of the input signal mixed with the residual signal are attenuated by the inevitable high frequency rolloff of the controller. Low frequency components of the input signal provided to the sound generator, on the other hand, are attenuated by the cancellation effect of the noise cancellation system. Although some further filtration may be required, the low frequency components of the input signal provided to the controller and the high frequency components of the signal provided to the sound generator are retained, generally creating an overall balance of the input signal.

BRIEF DESCRIPTIONS OF THE DRAWINGS

A preferred exemplary embodiment of the present invention will hereinafter be described in conjunction with the appended drawings, wherein like designations denote like elements and:

FIG. 1 illustrates one embodiment of the headset incorporating a noise cancellation system according to various aspects of the present invention;

FIGS. 2A–B depict front and sectional side views of one of the earpieces of the headset of FIG. 1, respectively;

Figure 9A:
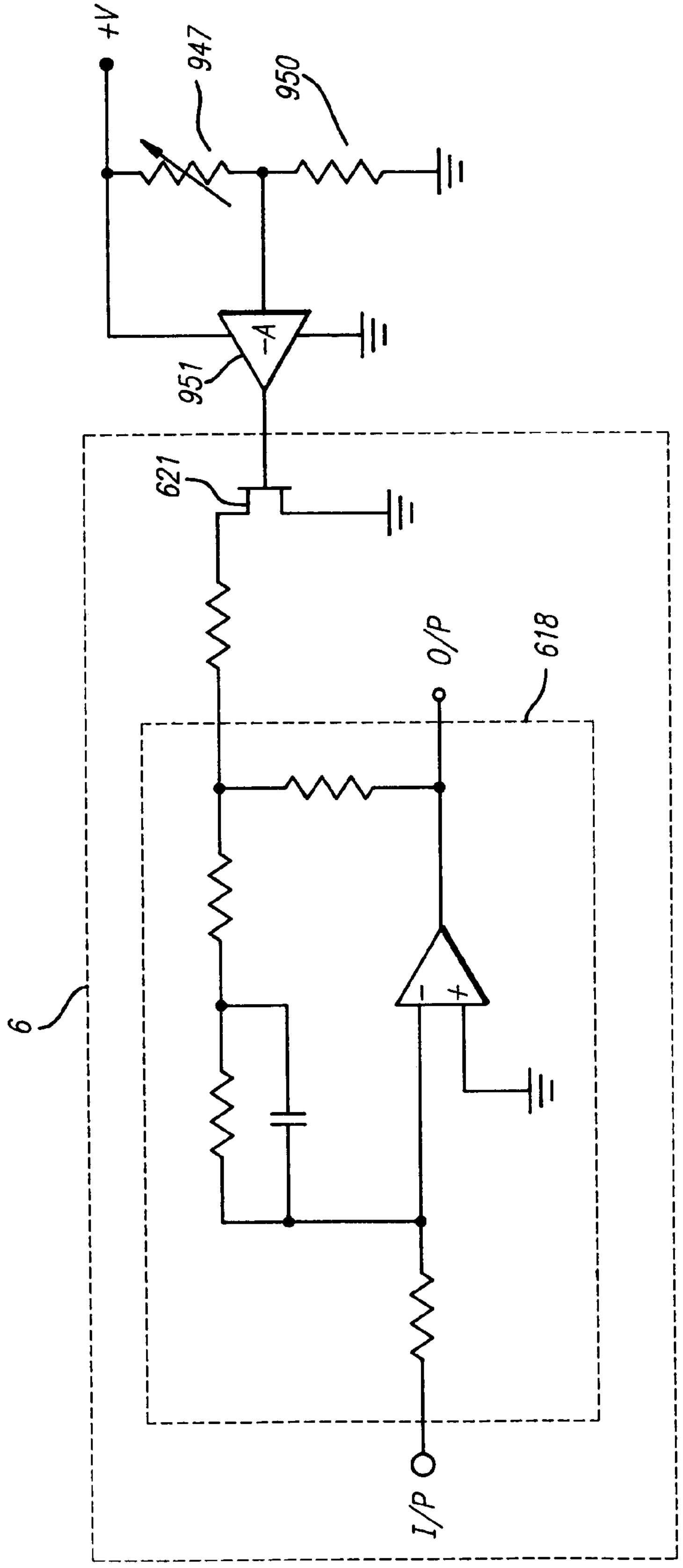
Figure 9B:
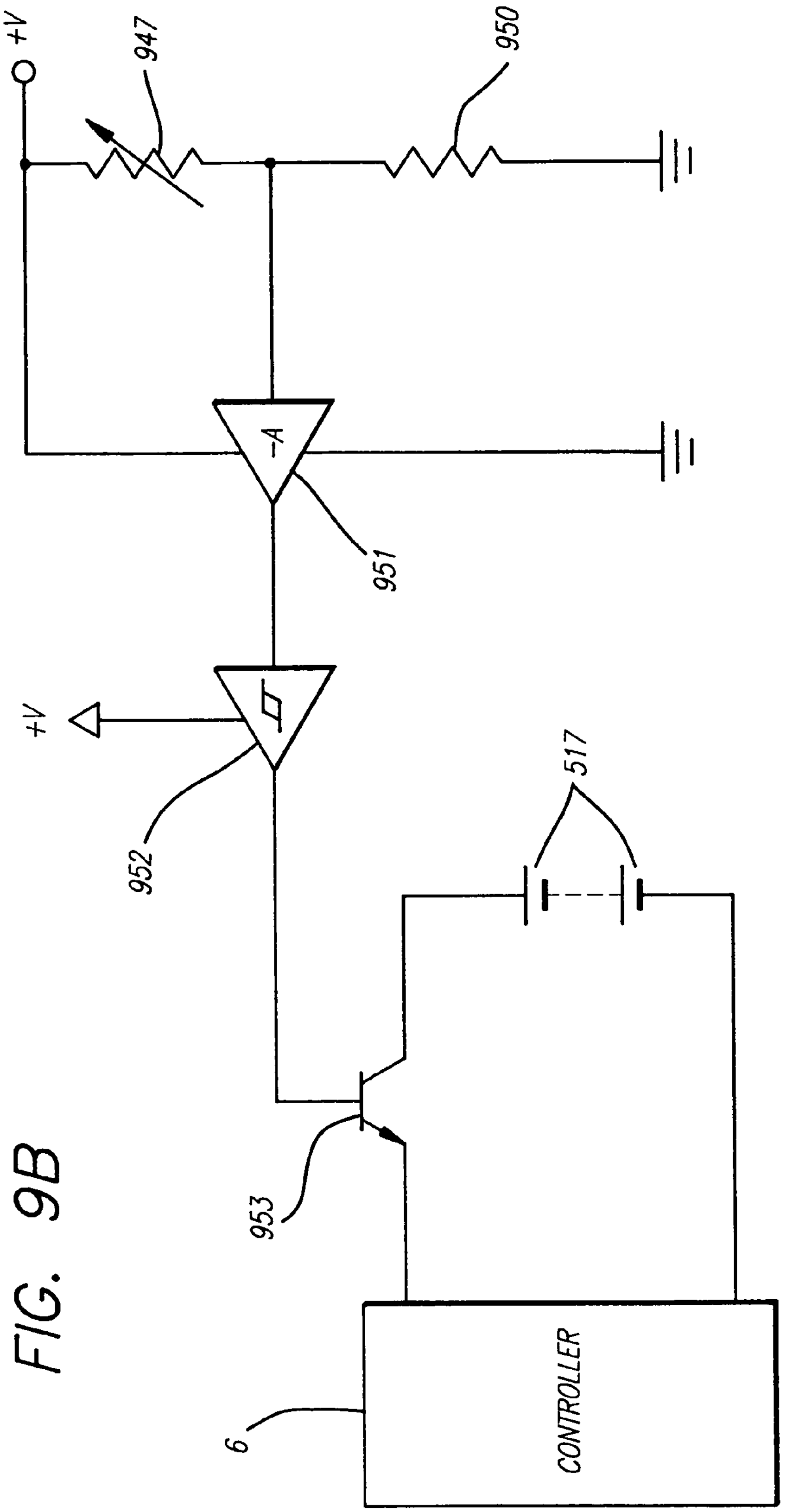
Figure 10:
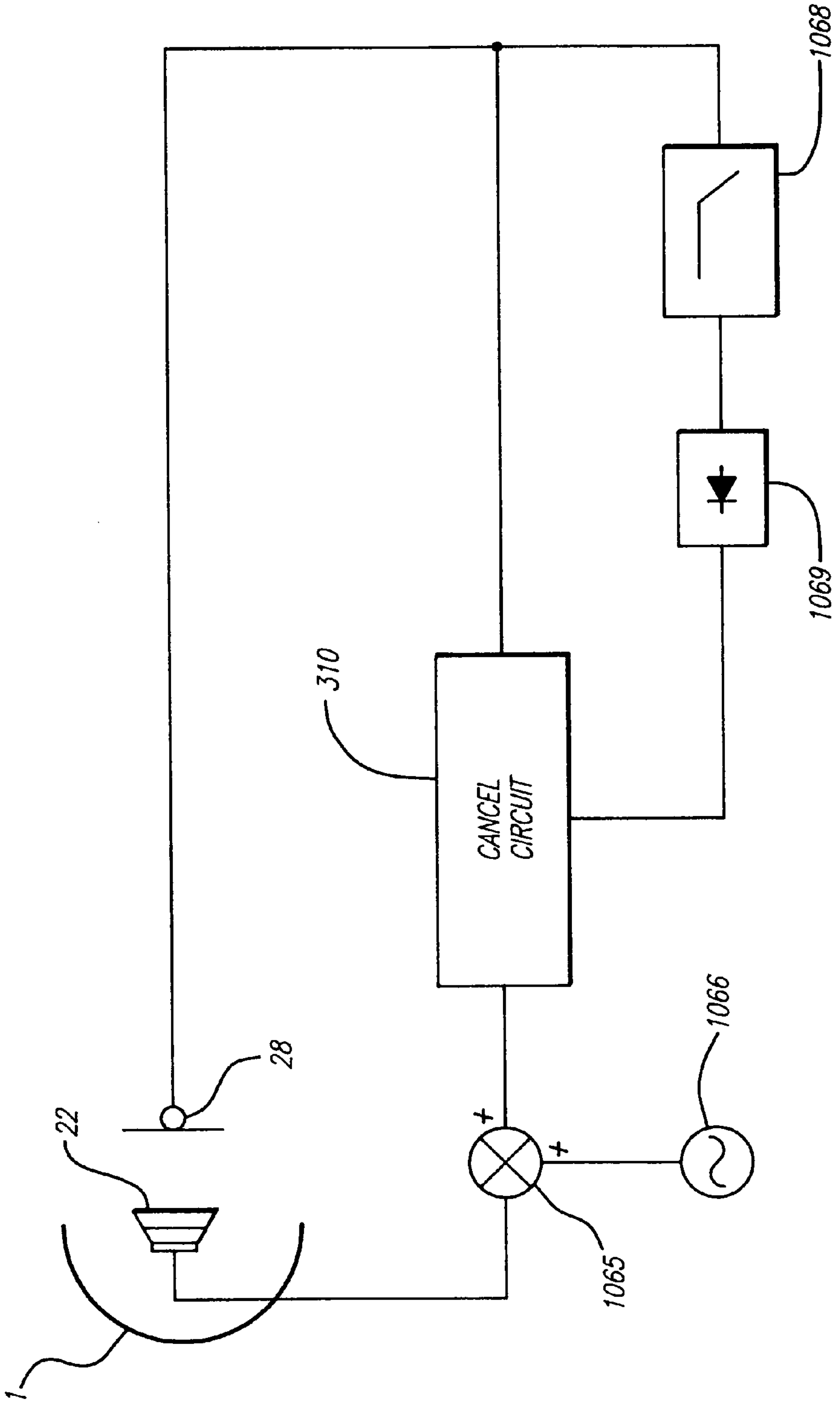
Figure 11:
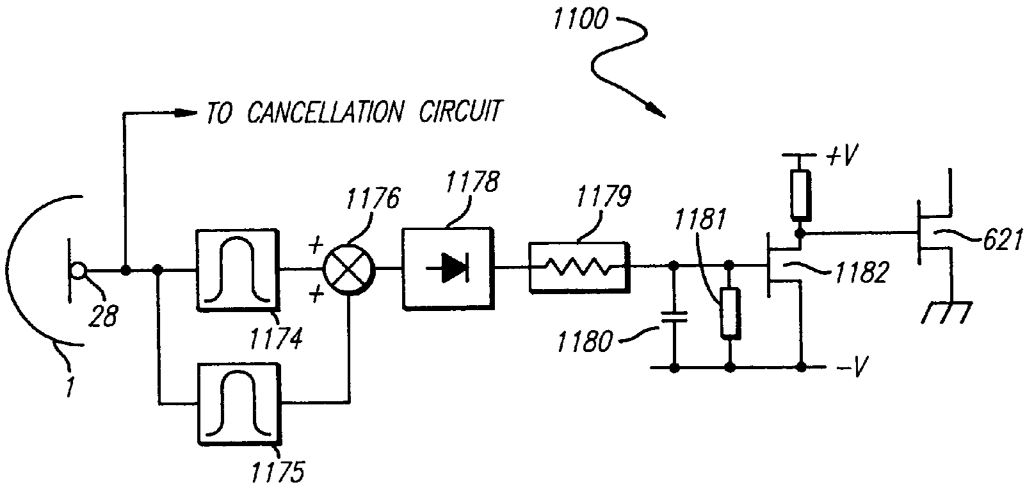
Figure 12:
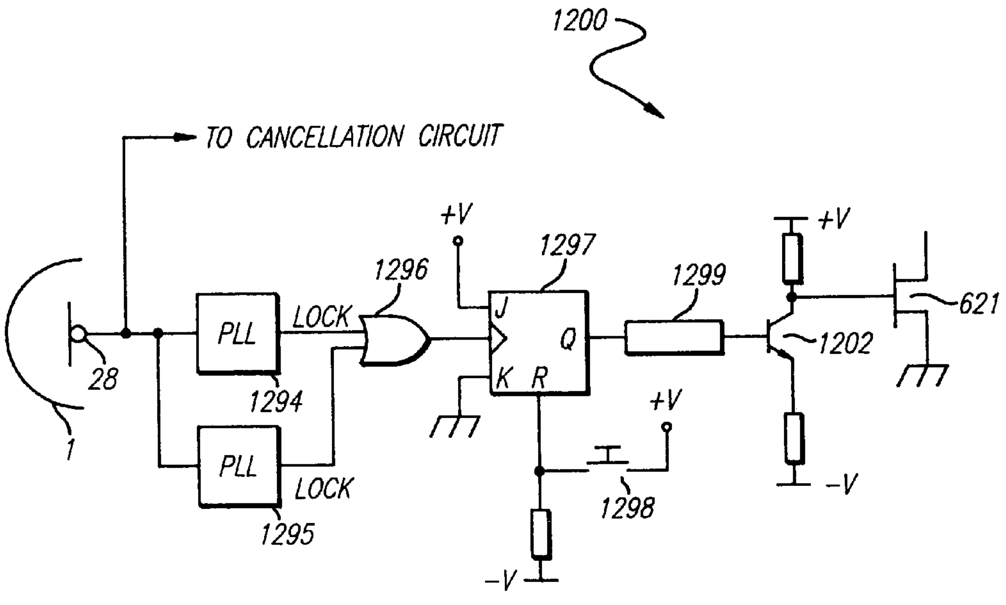
Figure 13:
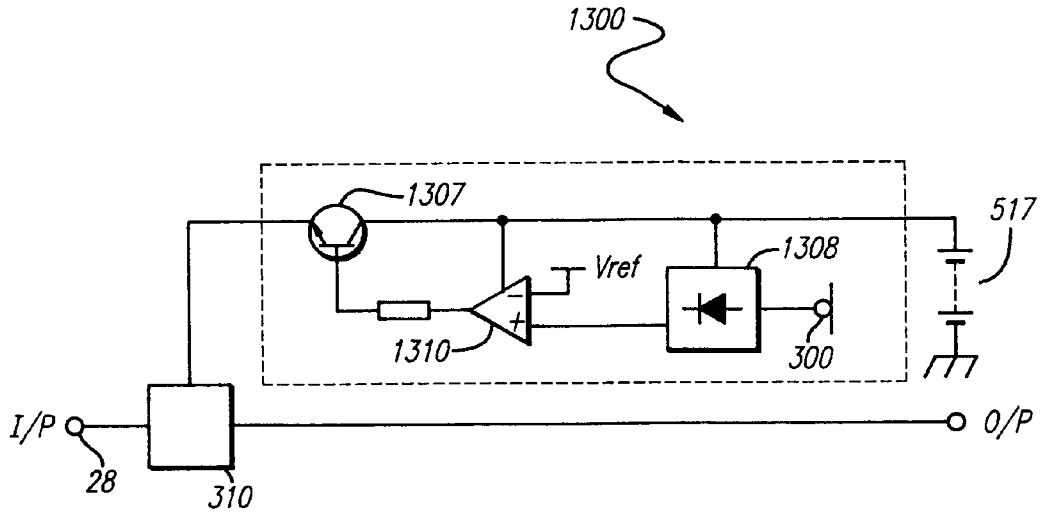
Figure 14:
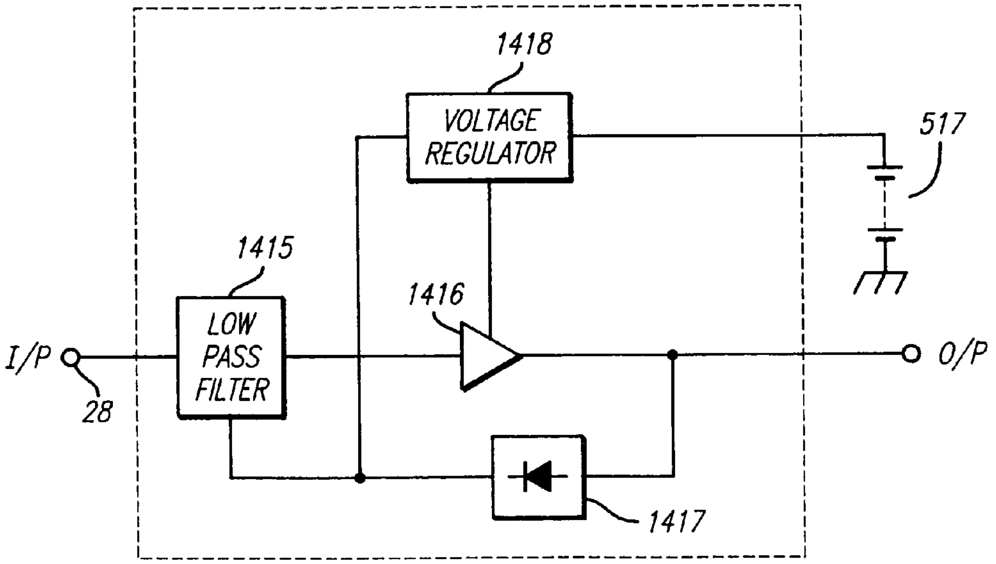
Figure 15:
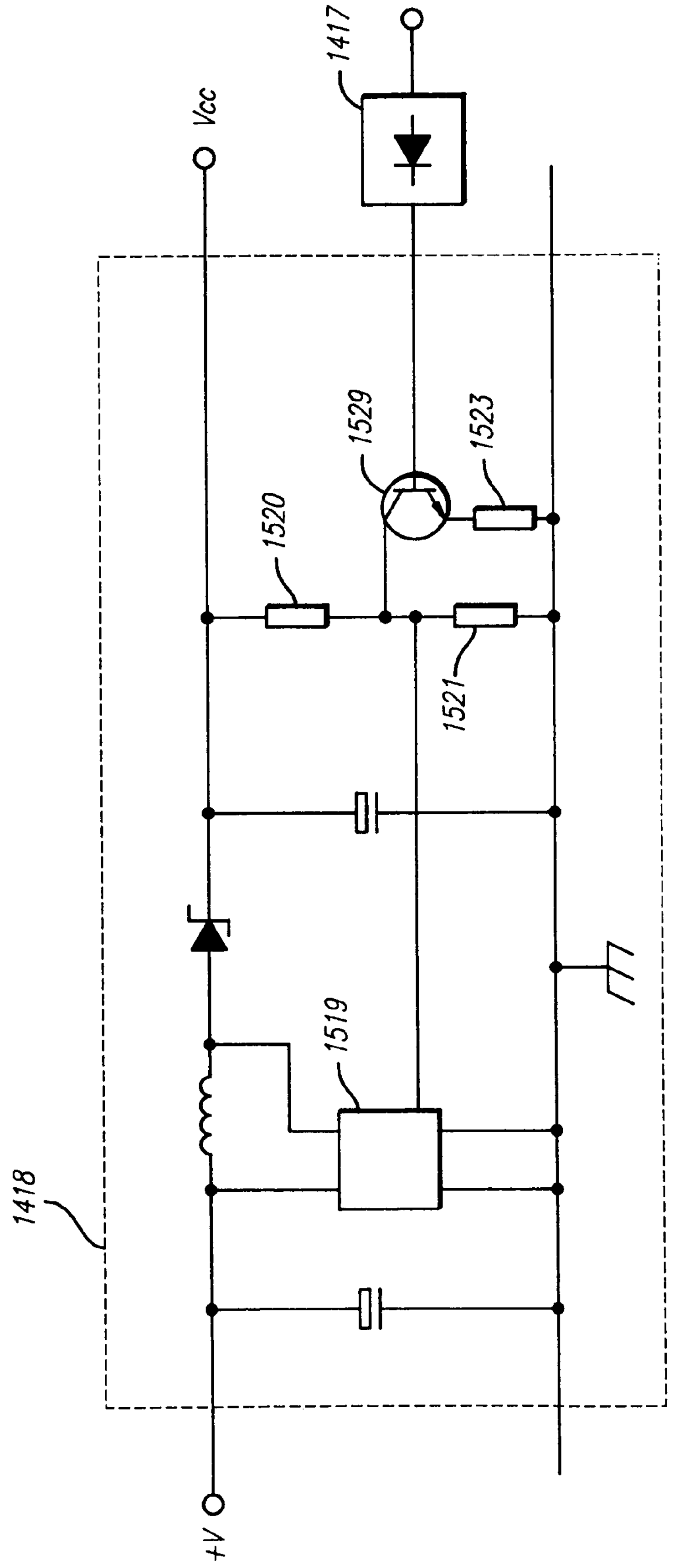
Figure 16:
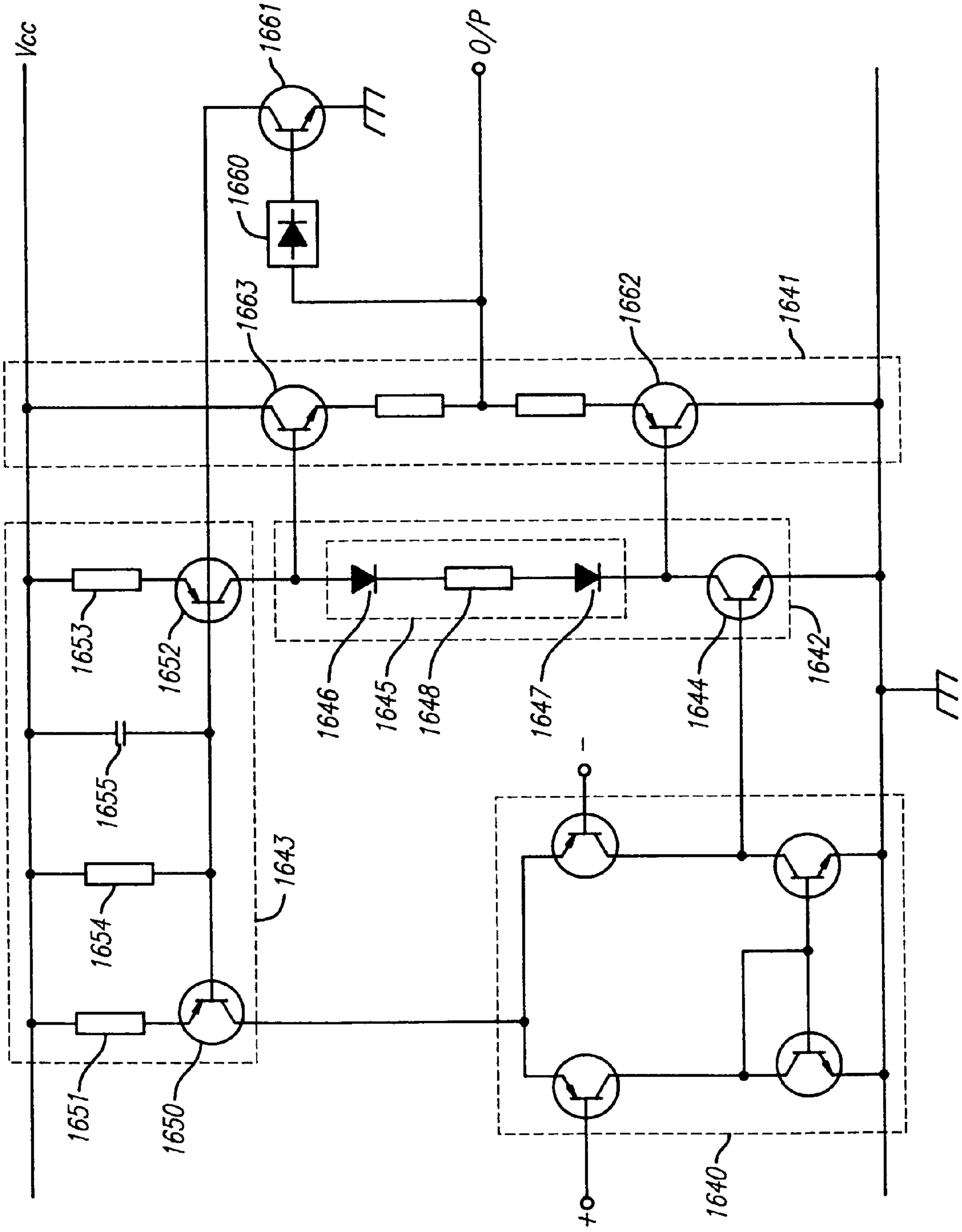
Figure 17:
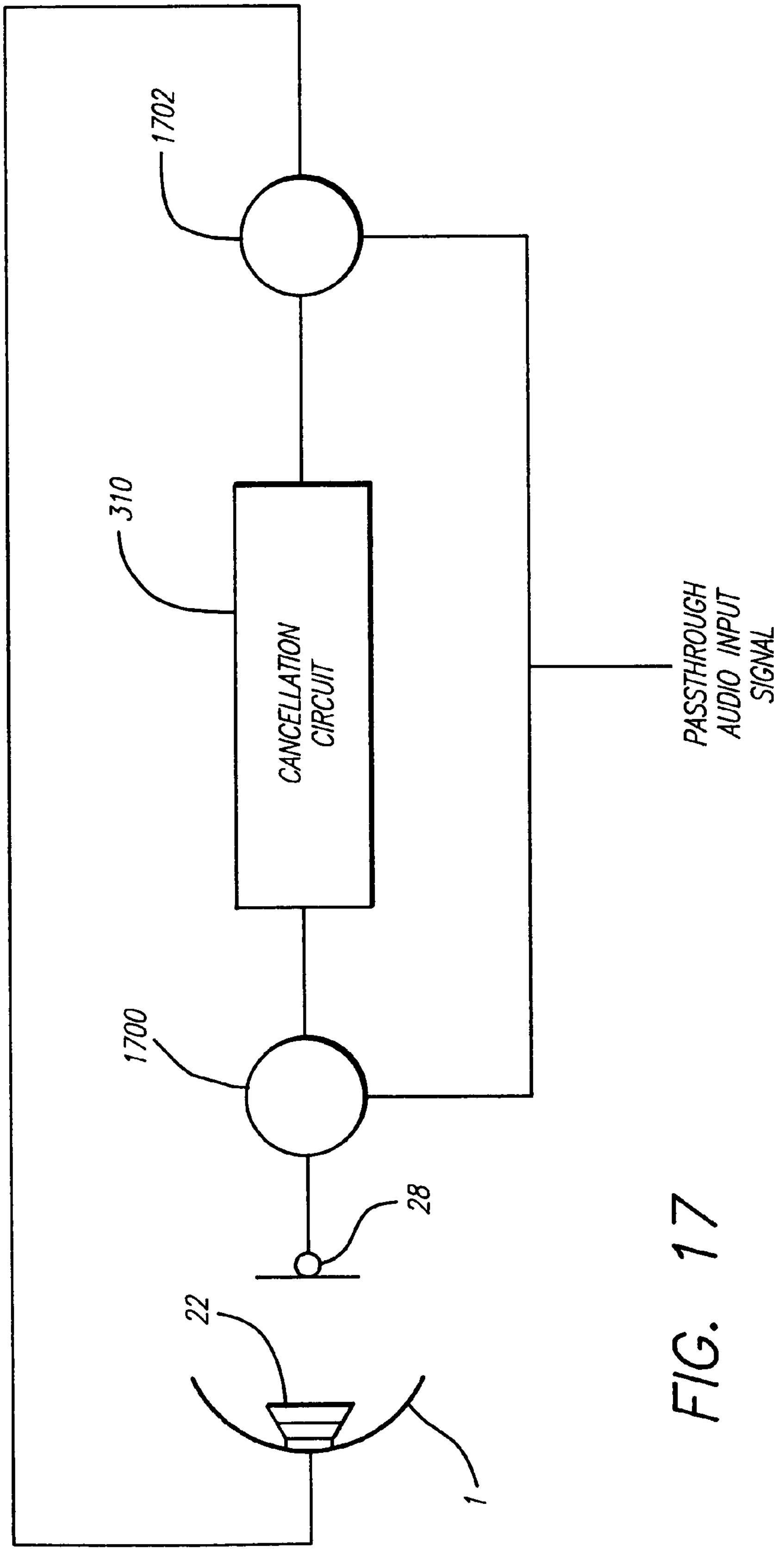
Figure 18:
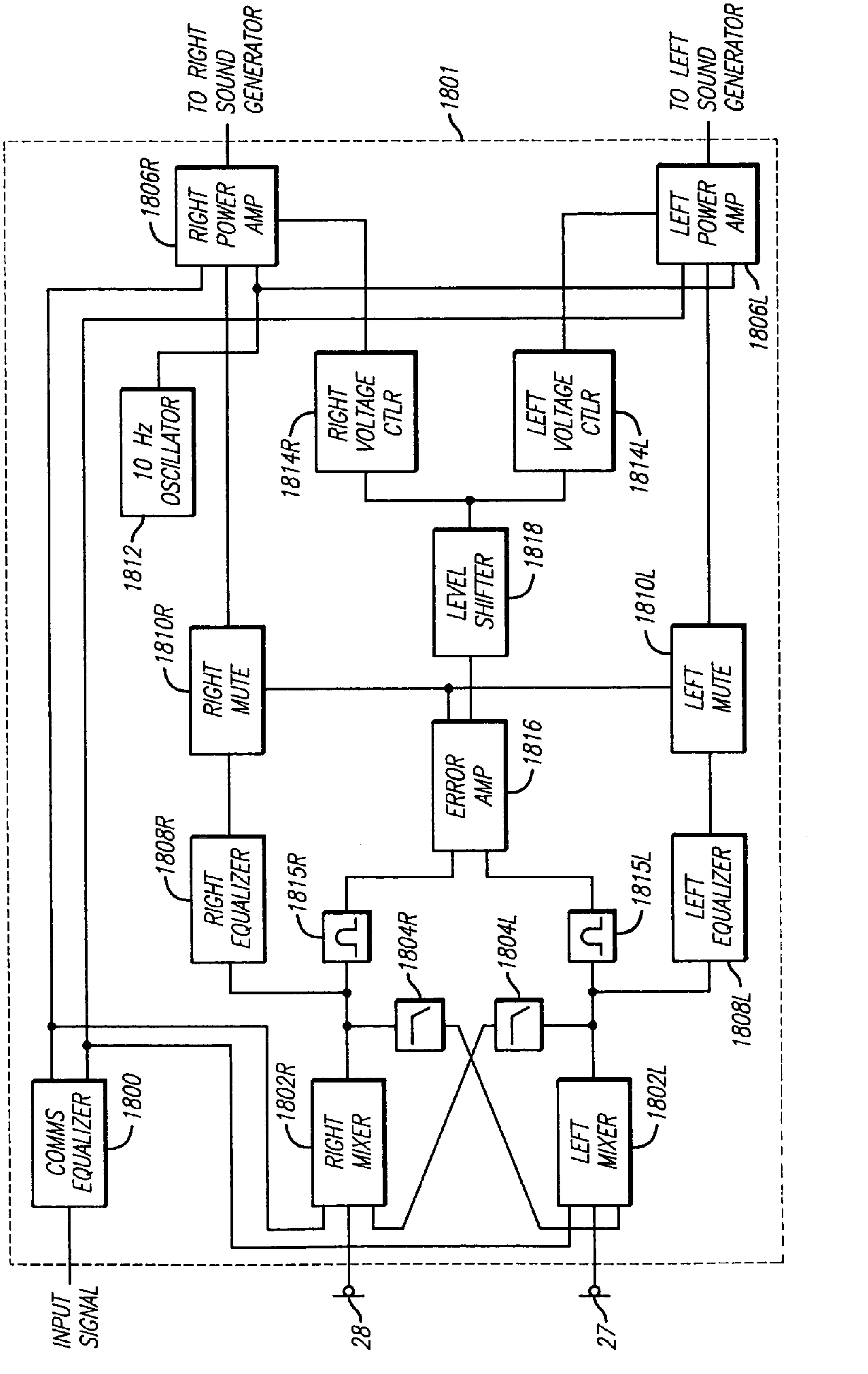
Figure 19:
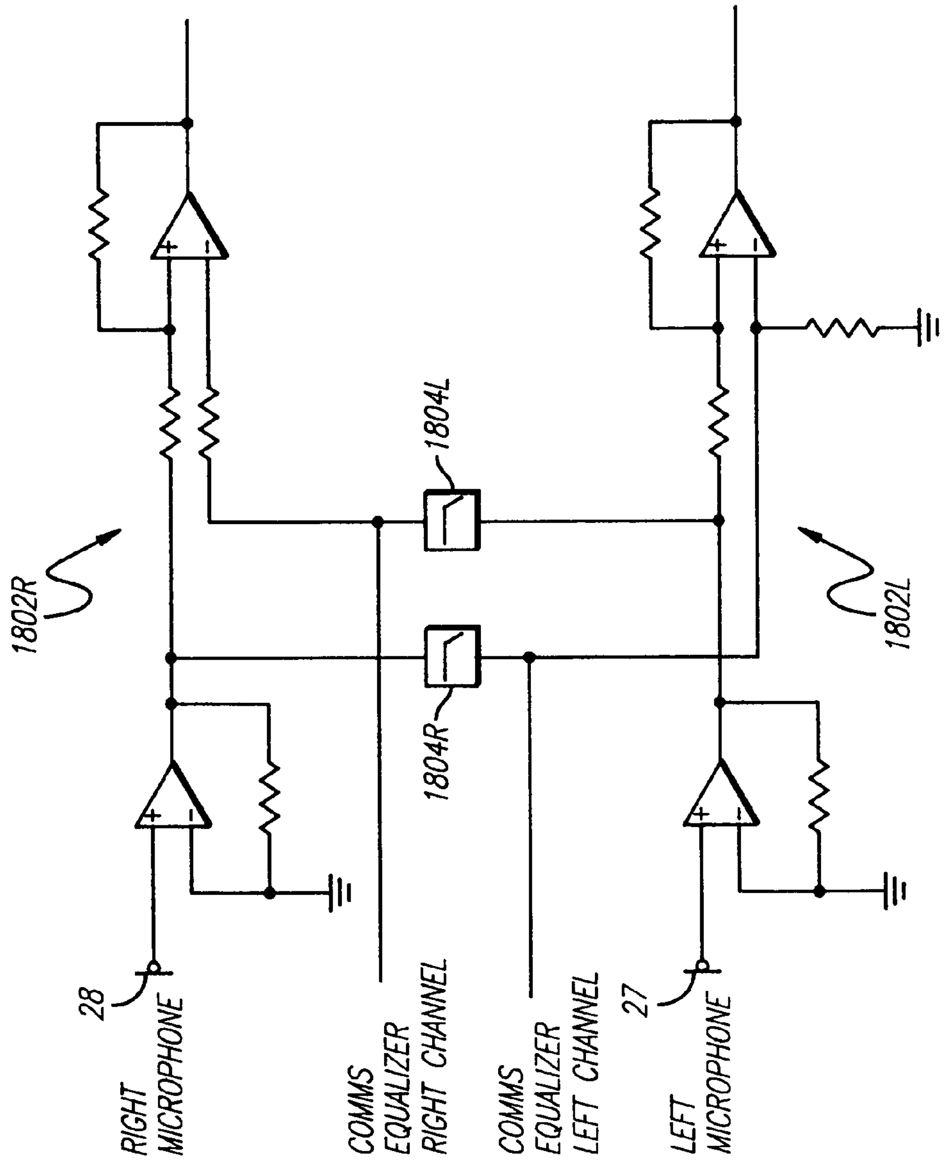
Figure 20:
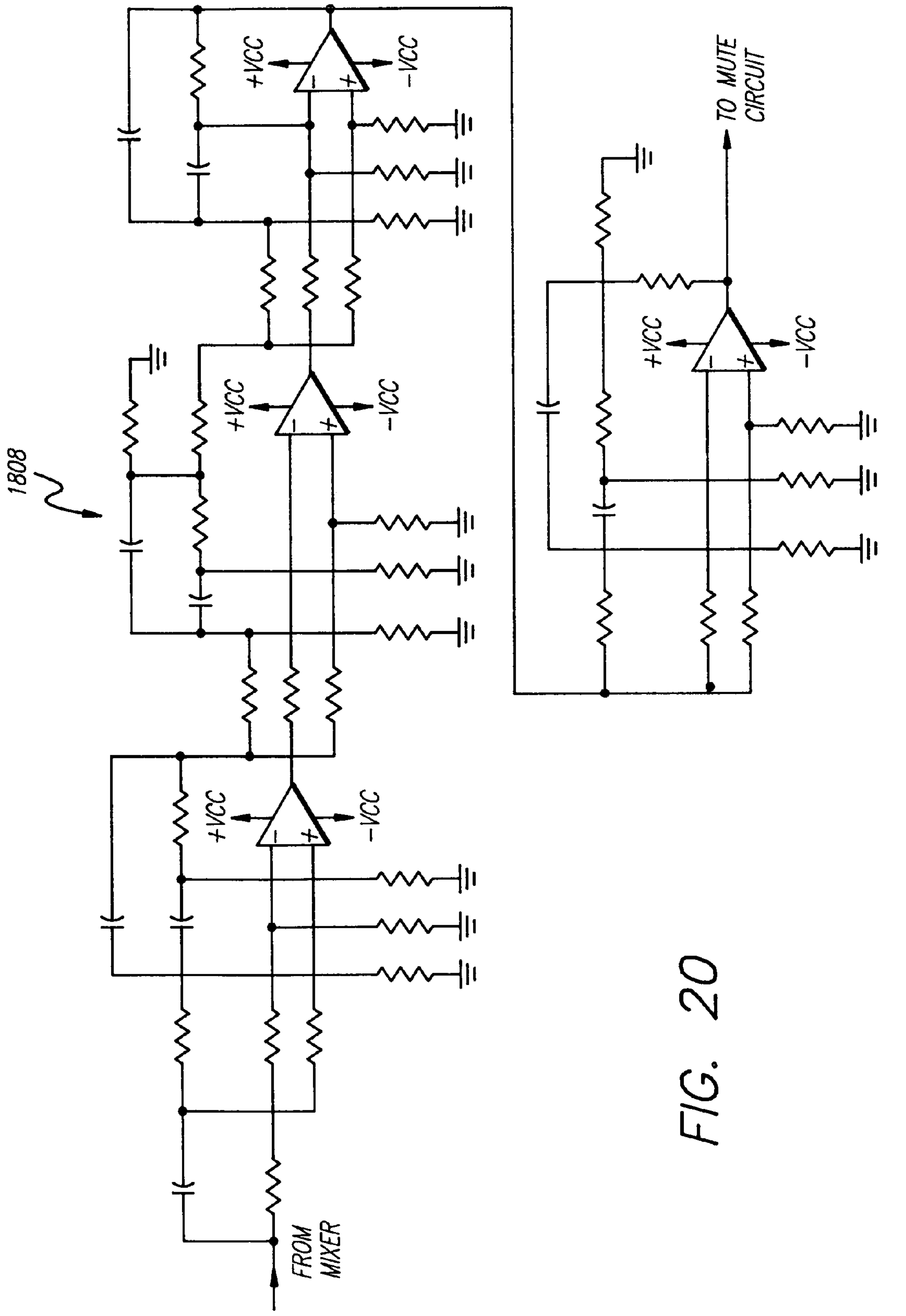
Figure 21:
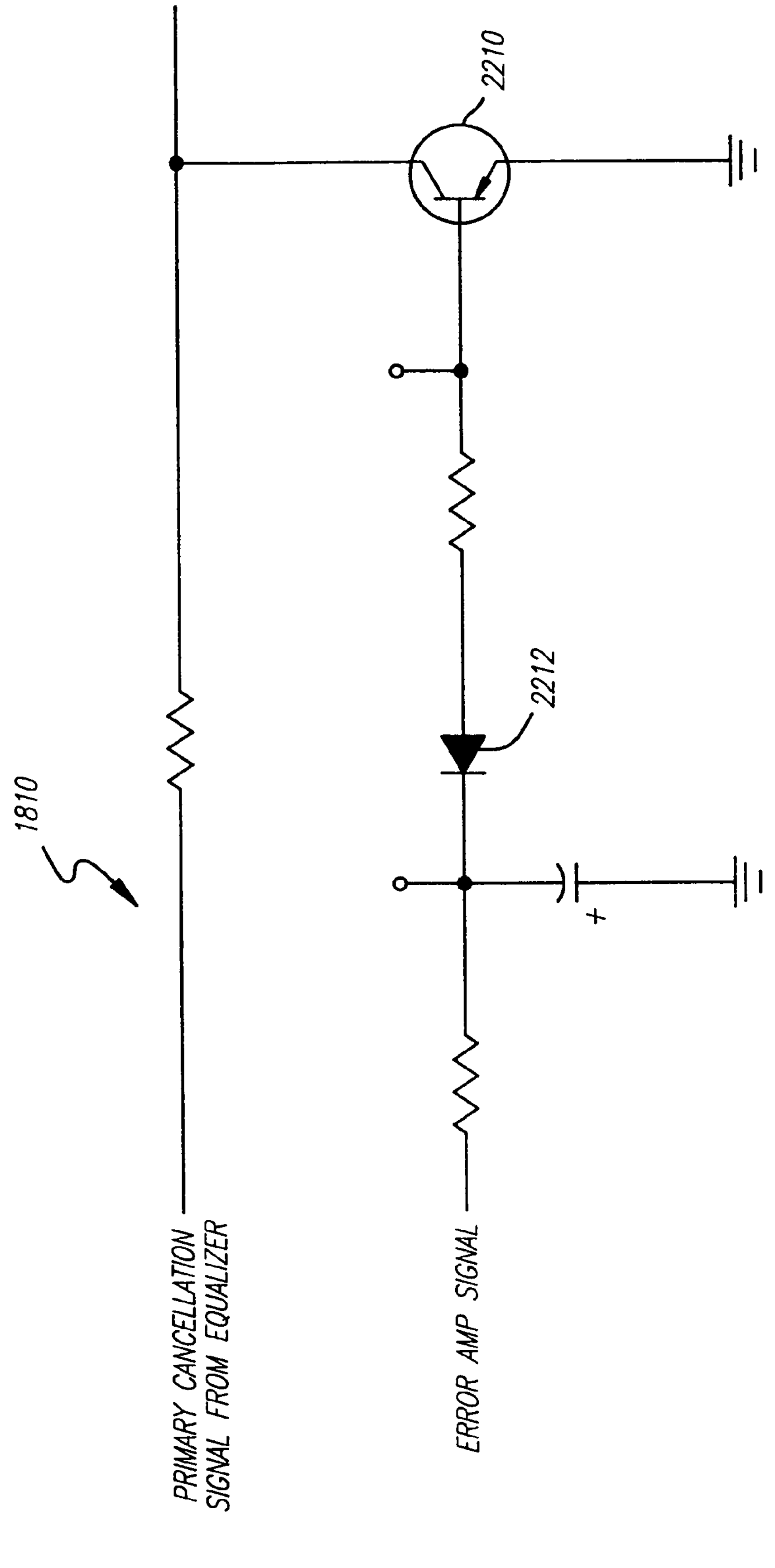
Figure 22:
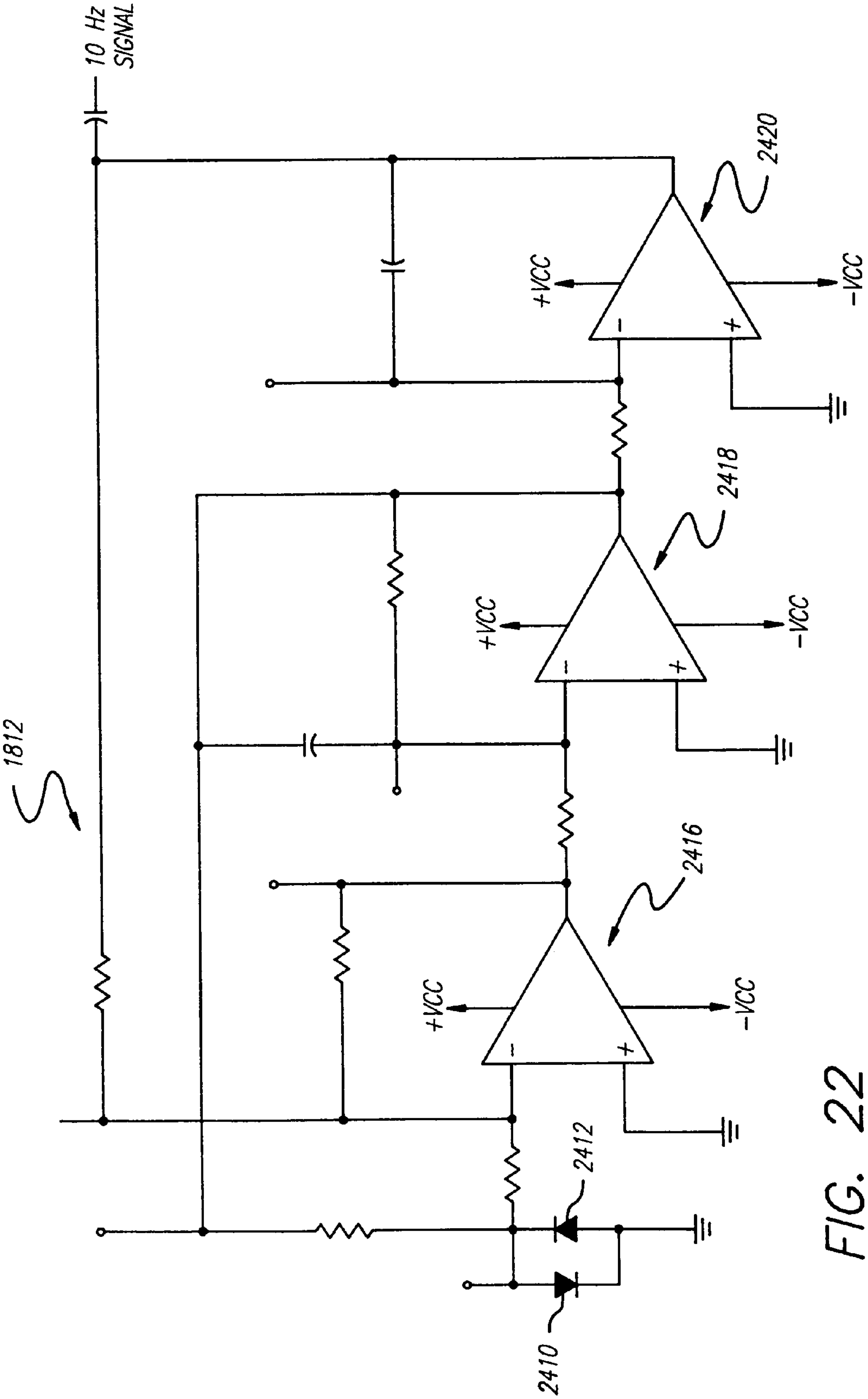
Figure 23:
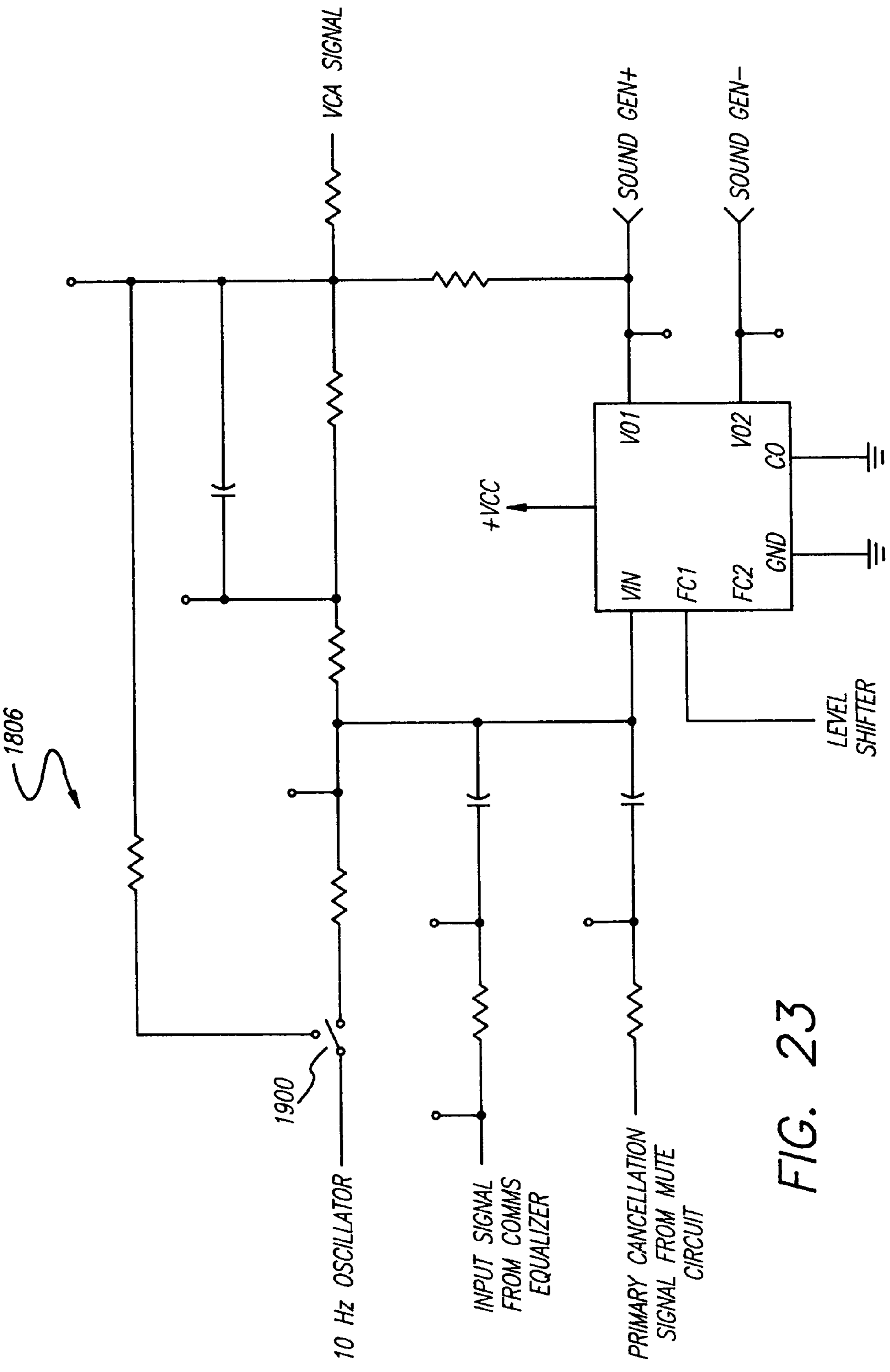
Figure 24:
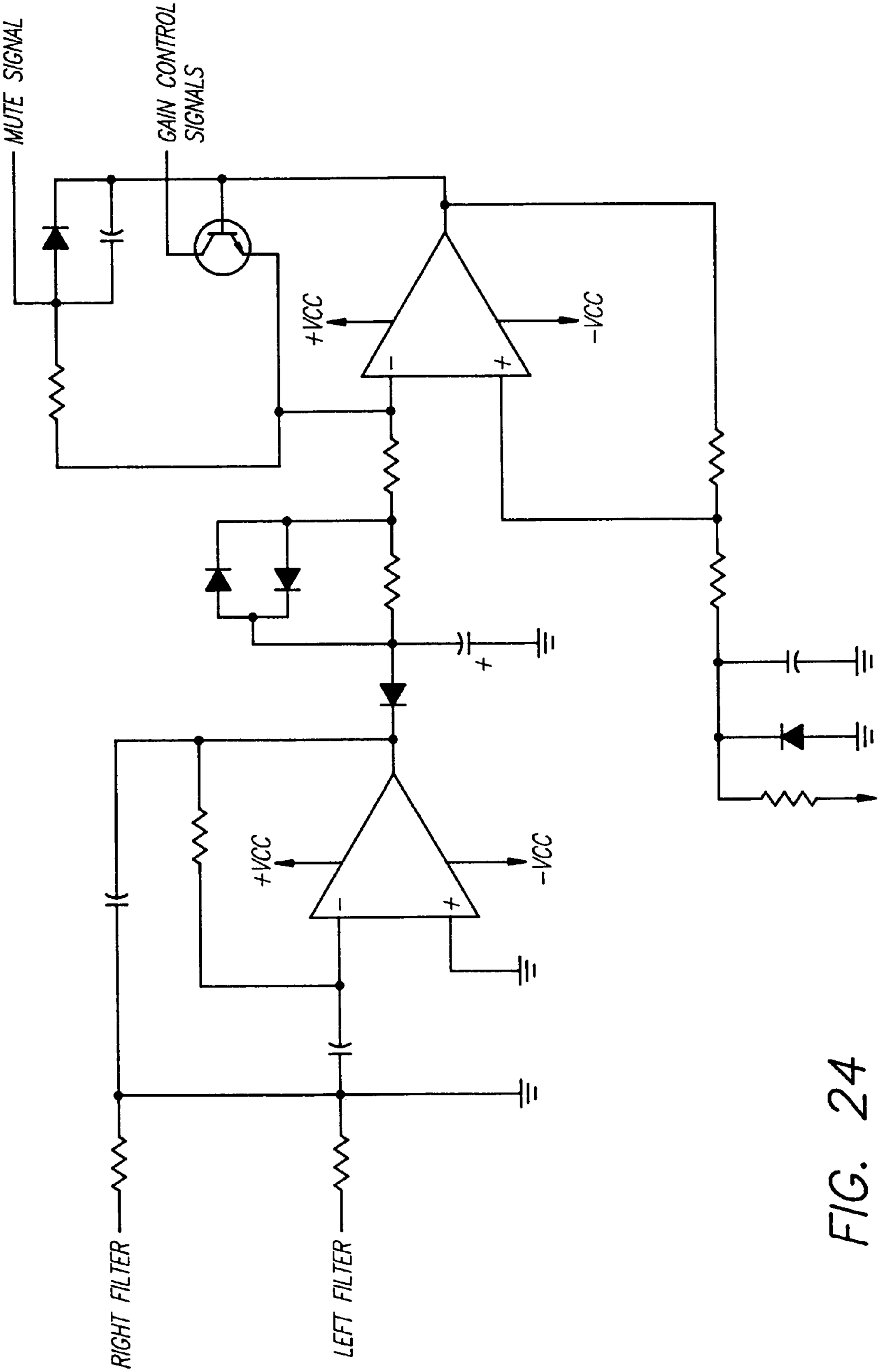
Figure 25:
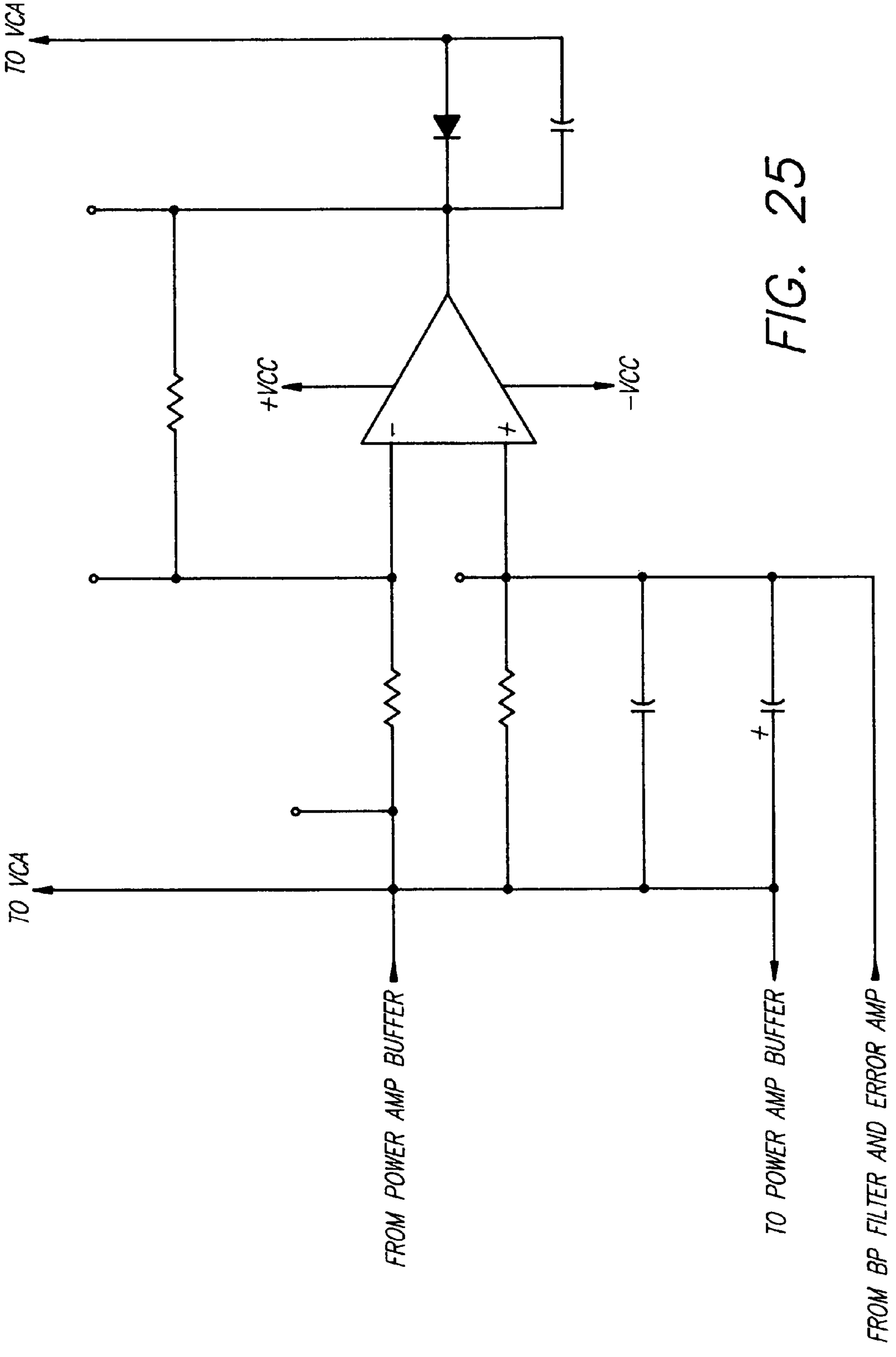
Figure 26:
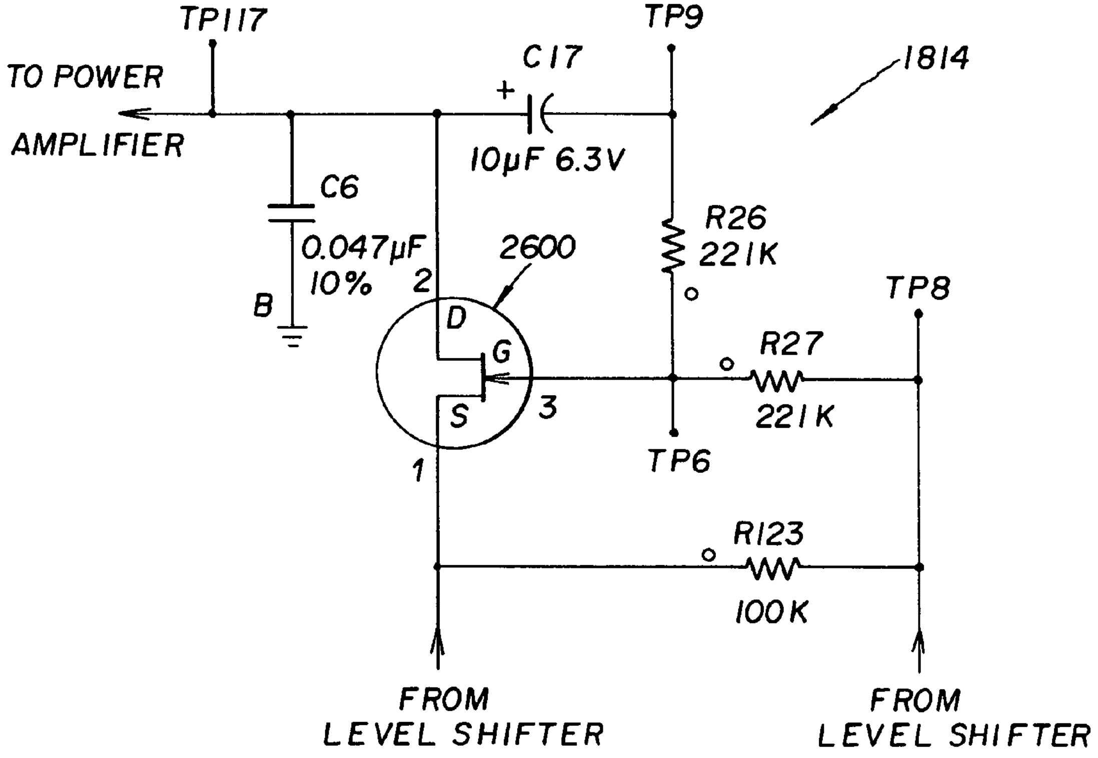

FIGS. 9A–B are schematic diagrams of variable gain and pressure sensitive noise cancellation control systems according to various aspects of the present invention;

FIG. 10 is a block diagram of a headset noise cancellation system using a subsonic acoustic signal according to various aspects of the invention;

FIG. 11 is a schematic and block diagram of a variable gain control system for a noise cancellation system;

FIG. 12 is a schematic and block diagram of the variable gain control system for a noise cancellation system employing phase lock loop circuits;

FIG. 13 is a schematic and block diagram of a control system for a noise cancellation system including power control circuitry;

FIG. 14 is a schematic and block diagram of a control system for a noise cancellation system including variable power control circuitry;

FIG. 15 is a schematic diagram of the switched mode voltage generator suitable for use in the system to FIG. 14;

FIG. 16 is a schematic diagram of a power amplifier having variable voltage;

FIG. 17 is a block diagram of a noise cancellation circuit according to various aspects of the present invention having a pass-through audio input signal;

FIG. 18 is a block diagram of a noise cancellation system controller according to various aspects of the present invention suitable for use in a headset;

FIG. 19 is a schematic diagram of an exemplary mixer circuit for use in the controller of FIG. 18;

FIG. 20 is a schematic diagram of an exemplary equalizer for use in the controller of FIG. 18;

FIG. 21 is a schematic diagram of an exemplary meeting circuit suitable for use in the controller of FIG. 18;

FIG. 22 is a schematic of an exemplary oscillator suitable for use in the controller of FIG. 18;

FIG. 23 is a schematic diagram of an exemplary power amplifier suitable for use in the controller of FIG. 18;

FIG. 24 is a schematic diagram of an exemplary error amplifier suitable for use in the controller of FIG. 18;

FIG. 25 is a schematic diagram of an exemplary level shift or for use in the controller of FIG. 18; and FIG. 26 is a schematic diagram of an exemplary voltage controller suitable for use in the controller of FIG. 18.

DESCRIPTION OF PREFERRED EXEMPLARY EMBODIMENTS

Embodiments of the present invention are described, by way of example, with reference to the accompanying drawing. The term headset as used herein includes but is not limited to ear defenders, headphones, earphones and telephone headsets and handsets. The term noise as used herein includes both periodic and non-periodic acoustic signals, including vibrations in solids and fluids.

Figure 1:
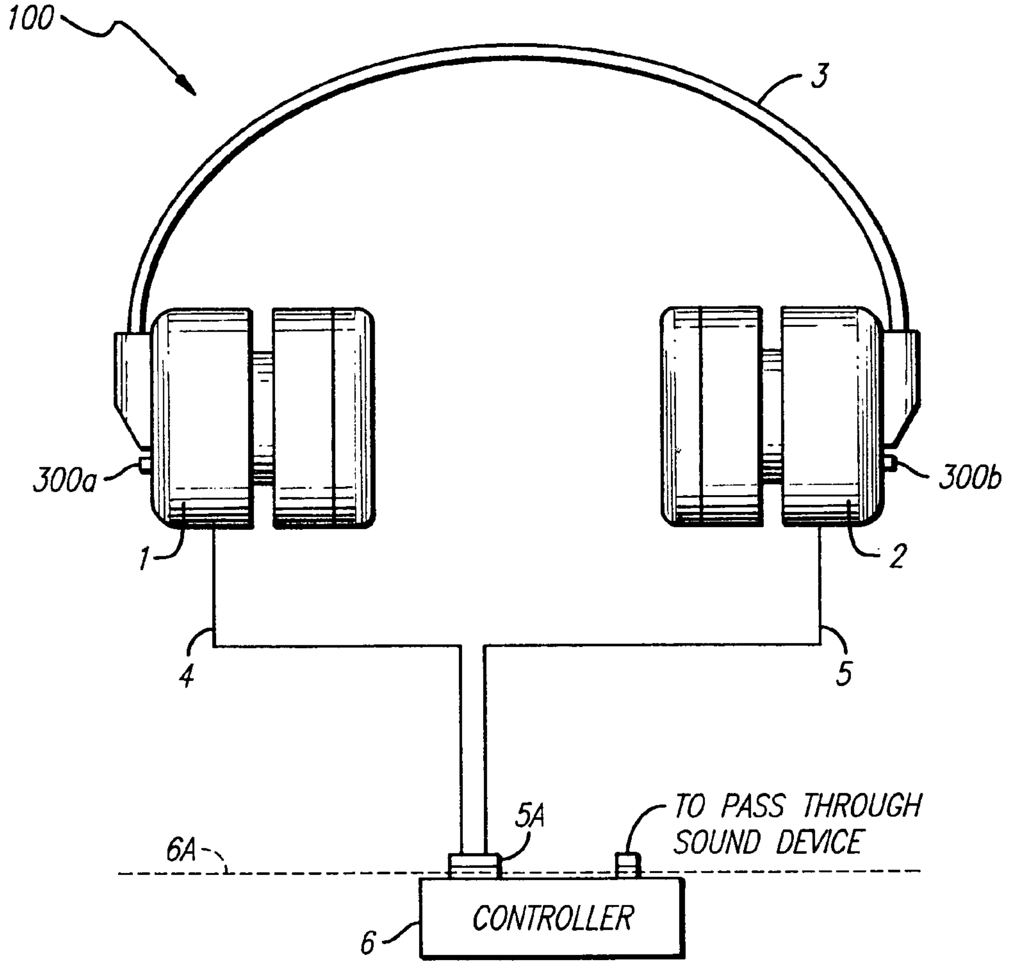

Referring to FIG. 1, a noise cancellation headset 100 suitably comprises a first earpiece 1 and a second earpiece 2, coupled by a resilient headband 3. External microphones 300*a, b* are mounted on the outside of earpieces 1, 2, suitably beneath headband 3. Earpieces 1 and 2 enclose respective sound generating units and internal microphones (not shown), which are electrically coupled by respective groups of wires 4, 5 to a controller 6. Controller 6 may be formed integrally with one or more of earpieces 1 and 2, headband 3 or otherwise one or more of the other components to form a unitary headset. Preferably, however, controller 6 is constituted as a separate unit to facilitate assembly, and, where batteries are employed as a power source, provide adequate space to accommodate the batteries.

Wires 4 and 5 are preferably removably coupled to controller 6 through a suitable connector 5*a*. If desired, controller 6 may also be connected, suitably through a conventional ⅛ inch audio jack 56, to a source of sound desired to be passed through headset 100 and communicated to the user. Exemplary pass through sound sources include such things as conventional consumer audio equipment such as radios, and tape or CD players, and intercom or other communication systems.

A separate controller 6 facilitates incorporating controller 6 into another piece of equipment or fixture, such as, for example, into the armrest or headrest of an aircraft seat (generally indicated in FIG. 1 as 6*a*), where desired. Use of a separate controller unit also makes the portion of the system worn on the user's head lighter and more comfortable. Further, removable portion of the system is less expensive. In contexts where headset units are issued at various times to numerous different users for use with a given installed controller, such as in airline passenger use, this can be a significant advantage. In the context of airline use, the conventional aircraft audio signals would be the pass through signal source to controller 6.

Controller 6 may comprise a virtual earth controller. Examples are described in PCT Application No. GB91-01399, filed on Jul. 28, 1992, by Active Noise and Vibration Technologies, Inc., et al., commonly assigned with the present invention. One aspect of a controller 6 such as described in the cited application is particularly adapted to canceling harmonically related tones in noise. Consequently, such a virtual earth controller 6 employs a synchronizing signal input, suitably derived from an appropriate synchronizing signal source, such as, for example, from a phase locked loop circuit fed with a signal from a microphone mounted outside the earpieces.

Controller 6 may alternatively comprise more sophisticated controllers, such as for example, filtered-X, or periodic controllers. A suitable filtered-X controller is described in U.S. Pat. No. 4,473,906, issued Sep. 25, 1984, to Warnaka, et al., and a suitable periodic controller is described in U.S. Pat. No. 4,654,871, issued Mar. 31, 1987, to Chaplin, et al. Various aspects of the present invention are also applicable to feedforward active noise control systems.

Figure 2A:
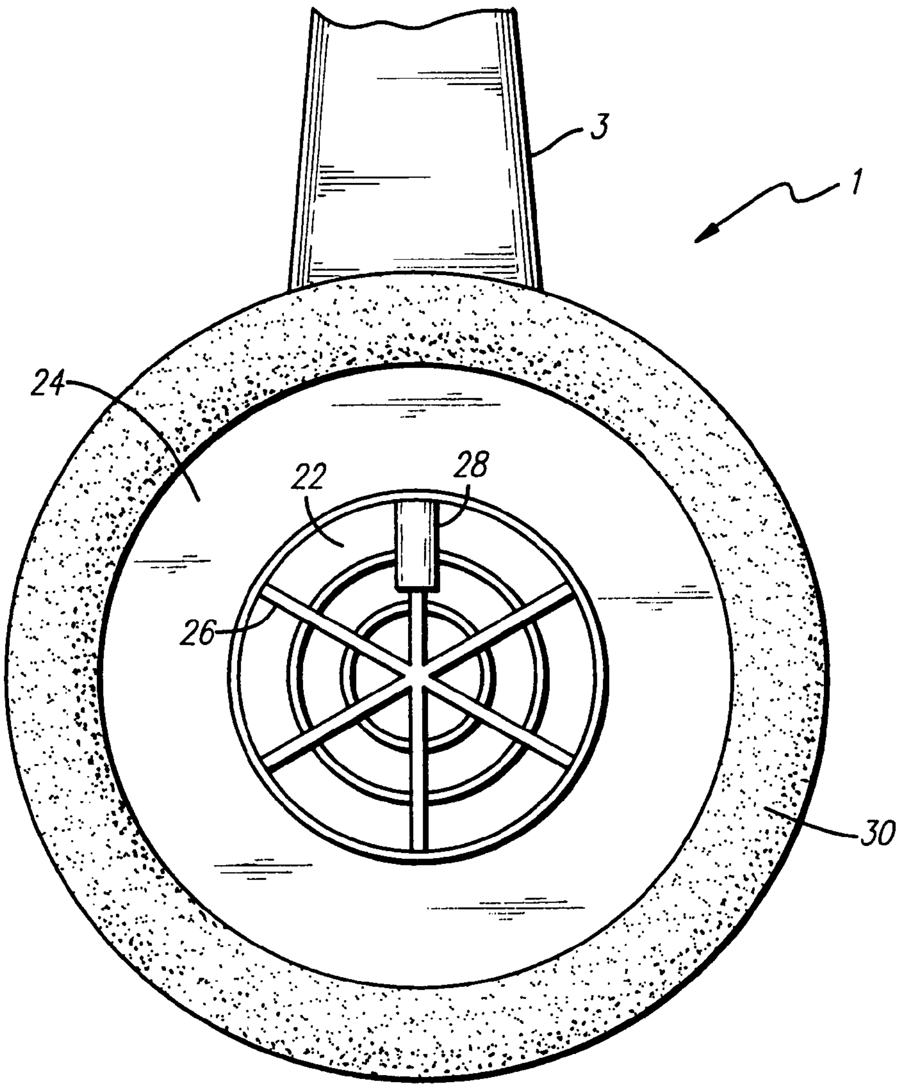

Referring now to FIG. 2A, each earpiece 1, 2 suitably includes a sound generator 22, a shell having an inner, suitably concave, surface 24, a grille 26, a microphone 28, and a cushion 30. Suitably, earpieces 1 and 2 are substantially identical; thus, only one earpiece (1) is described herein. Inner surface 24 and cushion 30 form an inner cavity within earpiece 1. Sound generating unit 22 is positioned behind a perforation (orafice) formed in inner surface 24, and the perforation is covered with grille 26. Grille 26 is suitably composed of plastic or metal, and typically imparts certain acoustic properties to the sound system to achieve the desired acoustic response, as well as serving a protective function.

Sound generator 22 receives a drive signal comprising suitable cancellation from controller 6 (and, if desired, pass-through input signals) and transduces them into mechanical vibrations. These mechanical vibrations generate soundwaves which propagate through grille 26 and into inner cavity to the user's ear.

Foam cushion 30 is affixed, suitably coaxially, to the perimeter of the inner surface 24 of earpiece 1. Foam cushion 30 is preferably annular, though it is contemplated that cushion 30 may be designed otherwise, e.g. it may cover sound generator 22 and inner surface 24. Foam cushion 30 provides padding between earpiece 1 and the user's head, and is lightly clamped between the user's ear and earpiece 1. Typically, the nature of foam cushion 30 is such that it does not provide an acoustic seal between earpiece 1 and the user's head or ear. Several aspects of the present invention, however, are applicable to headsets equipped with a cushion that does form an acoustic seal between the headset and the user's head.

According to one aspect of the present invention, microphone 28 may be positioned on either the side of grille 26 which is nearest sound generator 22 or which is nearest the ear. As shown in FIG. 2A, microphone 28 is suitably positioned offset (suitably radially) from the center of grille 26, and, more particularly, offset from the center of sound generator 22. Microphone 28 may be positioned in any direction from center of sound generator 22. In the preferred embodiment, however, microphone 28 is offset from center in the direction corresponding to the top of the user's head. While microphone 28 may also be disposed offset in directions corresponding to the bottom or sides of the earpiece 1, reception may be blocked by the user's ear covering microphone 28. The particular position of microphone 28 depends upon several acoustic parameters, such as the distance of sound generator 22 from the user's eardrum, the size of the inner cavity, the characteristics of grille 26 and other properties affecting the propagation of sound within inner cavity.

By effectively attenuating the cancellation sound sensed by microphone 28, the system can be made to more accurately cancel the sound received at the user's eardrum. Such attenuation can be effected by disposing microphone 28 offset from the center of sound generator 22. As the disposition of microphone 28 is laterally offset from the center of sound generator 22, the amplitude of the cancellation sound (anti-noise) detected by microphone 28 diminishes as compared to the amplitude of the anti-noise at a position aligned with the center of sound generator 22. Because the objective of the noise cancellation system is to minimize unwanted sound perceived by the user, the most advantageous position of microphone 28 is the position at which it most closely approximates the sound perceived by the user. This position varies according to the particular design of headset 100. The best position may suitably be determined by trial and error, or by mapping the sound pressure variations around grille 26 to determine the location exhibiting the frequency response most similar to that of the eardrum. By placing microphone 28 at a suitable location offset from the center of grille 26, the sound perceived by the user may be approximated without the problems associated with inserting a microphone into the ear canal of the user.

Alternatively, attenuation can be effected with microphone 28 positioned near grille's 26 center, but shielded from sound generator 22. For example, if the center of grille 26 is a solid continuous plate, microphone 28 may be mounted on the center of grille 26 if the center plate sufficiently shields microphone 28 to accurately simulate the noise perceived at the user's eardrum.

Figure 2B:
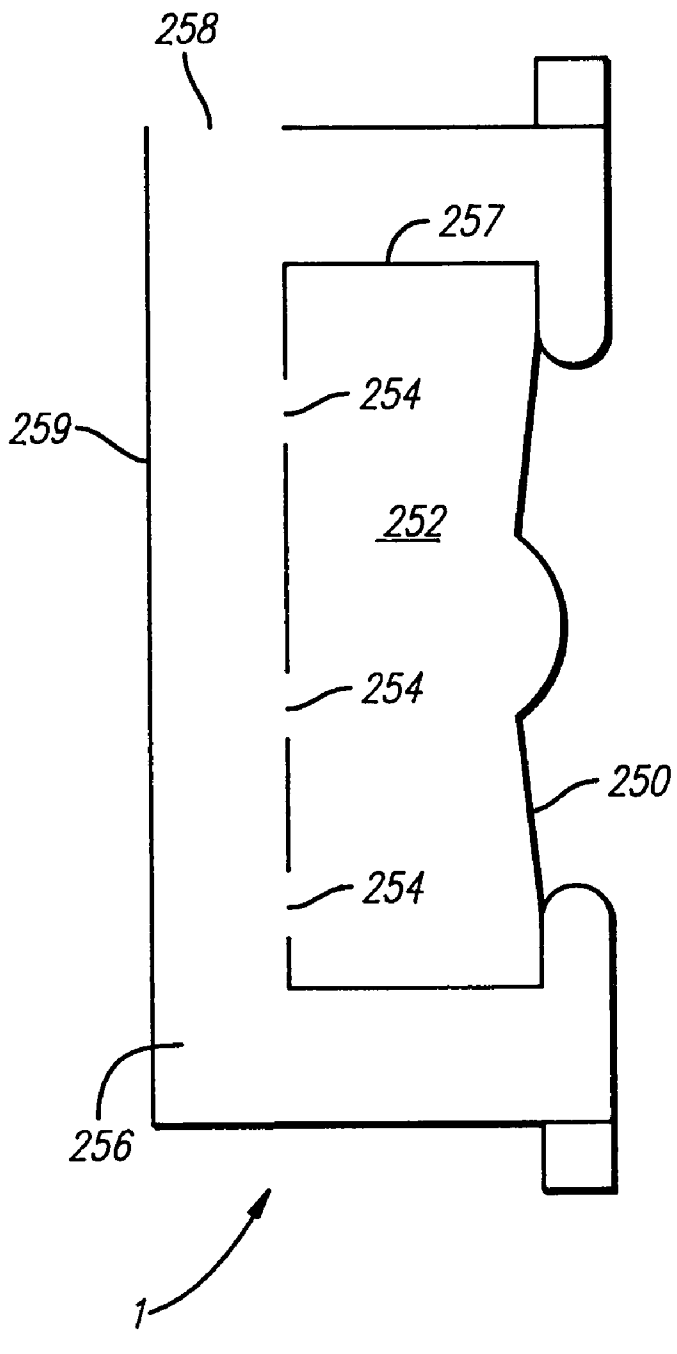

Referring now to FIG. 2B, earpiece 1 having an open back to improve low frequency response suitably includes an outer shell 259, and an inner wall 257 separated from outer shell 259 by an air space 286. Sound generator 22 in disposed with inner wall 257, and includes a diaphragm 250. Wall 257 forms a chamber 252 behind diaphragm 250. The back of chamber 252, i.e. wall 257, includes perforations 254 to allow air in chamber 252 to move in and out of chamber 252 and into space 256 formed between outer shell 259 and the back of chamber 252 (wall 257). Perforations 258 are formed in the side of outer shell 259, equalizing the air pressure between chamber 252, space 256 between chamber 252 and earpiece 1, and the ambient air.

Alternatively, outer shell 259 may be solid, and comprise a forward lip for disposition proximate the user's ear, a rear portion, and a transverse portion intermediate to the lip and rear portions, radially inset from the lip. Apertures may be formed through shell 259 communicating with the interior cavity behind sound generator diaphram 250 to enhance low frequency response of the earpiece. Since the apertures open in a transverse wall, inset from the lip of the shell, they are less susceptible to blockage.

Provision of perforations 258 on the side of earpiece 1 improves the low frequency response of headset 100. Perforations 258 are preferably limited in number and size to be acoustically closed to frequencies above a predetermined cutoff frequency. In the preferred embodiment, three 2-millimeter square perforations are provided to provide a cutoff frequency of about 1000 Hz. Thus, only frequencies below about 1000 Hz are improved.

Locating perforations 258 on the side of earpiece 1, particularly where the sidewall is inset from the periphery of the earpiece, reduces the likelihood of obstruction of perforations 258, improving the reliability of the characteristic transfer function. The sides of earpiece 1 are less susceptible to being inadvertently covered by the user's hands or another obstruction. Nonetheless, perforations on the side of earpiece 1 provide improved low frequency response.

Figure 3:
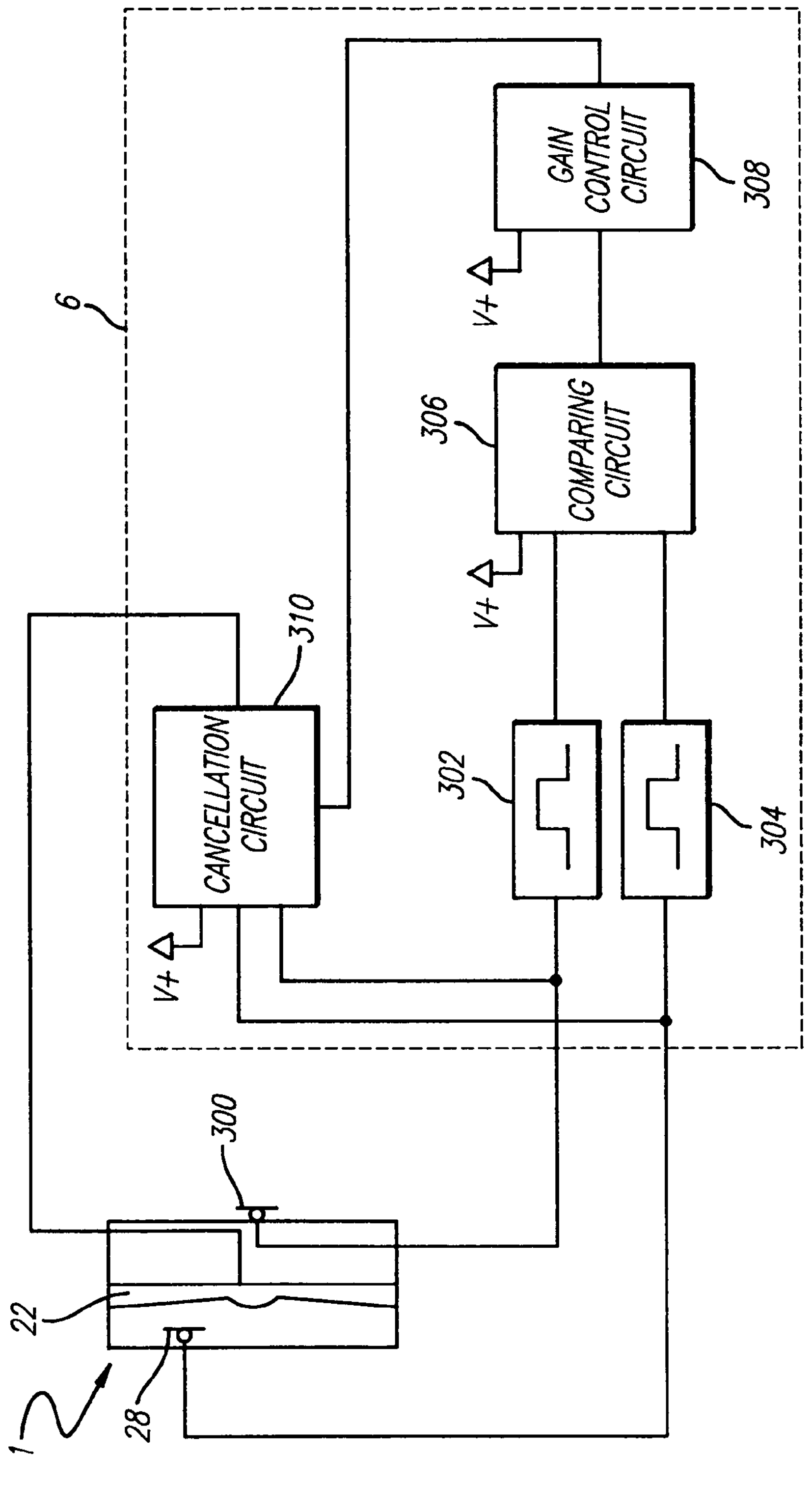
FIGS. 3 and 3A are block diagrams of control systems for the headset of FIG. 1.

Referring now to FIG. 3, controller 6 of FIG. 1 will be more fully described. Controller 6 suitably comprises: a suitable cancellation circuit 310, respective bandpass filters 302 and 304, a suitable comparing circuit 306, and suitable gain control circuitry 308. A residual signal from microphone 28 is applied to a cancellation circuit 310 in controller 6, which suitably processes the residual signal to develop a cancellation signal. The cancellation signal represents the residual signal, but inverted, and, if desired, suitably filtered and modified in accordance with a transfer function characteristic of the electromechanical properties of the system. The cancellation signal is then provided to sound generator 22 so that the resulting anti-noise corresponds to the sound detected by microphone 28, but inverted with respect to the detected sound.

To ensure sufficient cancellation, controller 6 provides a particular gain with respect to the amplitude of the signal. If the gain of controller 6 is too low, the cancellation signal is insufficient and the noise is less effectively canceled. Conversely, if the gain is too high, a feedback system destabilizes and lapses into oscillations. Similarly, the effectiveness of a feedforward system deteriorates if the gain is too high. Thus, the gain of controller 6 is preferably carefully regulated, with the goal of providing the highest possible gain without losing stability.

Controller 6 preferably employs automatic gain control circuits 308 to regulate the gain of the noise cancellation system. One aspect of the present invention utilizes the enhancement effect common to many feedback control systems. In virtual earth systems, for example, frequencies within certain enhancement frequency ranges are enhanced immediately before the system destabilizes. Generally, the enhancement effect occurs primarily within two ranges, a high frequency enhancement range and a low frequency enhancement range. Thus, as the gain is increased, soundwaves in the high and low enhancement ranges (hereafter referred to as the enhancement frequency ranges) are enhanced instead of canceled. As the gain is further increased, the system lapses into instability.

The enhancement frequency ranges are commonly well defined for a system, and the system is suitably designed to have a particular enhancement frequency range outside the cancellation bandwidth. The system may also be designed so that the degree of enhancement is proportional to the gain. In the exemplary embodiment of FIG. 3, an external microphone 300 is suitably mounted on the outside of earpiece 1. External microphone 300 provides an output signal corresponding to the noise field detected outside earpiece 1. The output signals of microphones 28 and 300 are applied to cancellation circuit 310 as feedback and feedforward signals, respectively, and through respective bandpass filters 302, 304, to comparing circuit 306. Bandpass filters 302, 304 each have a predetermined pass band, at least partially within the high enhancement frequency range, preferably with a center frequency suitably at approximately the center of the enhancement frequency range. In the present embodiment, only the high enhancement frequency range is monitored, although the low enhancement frequencies may be used instead or complementarily.

Comparing circuit 306 suitably includes a divider circuit, which comprises circuitry to divide the filtered internal and external high enhancement frequency signals to determine an indicia of the ratio of their respective amplitudes. Comparing circuit 306 suitably generates an output signal indicative of deviation from a predetermined threshold value. The threshold value is suitably set slightly above the indicia, e.g., enhancement value ratio value, associated with suitably stable operation of the system. The output of comparing circuit 306 is then suitably provided to gain control circuit 308, which suitably adjusts the gain of cancellation circuit 310 accordingly to maintain a given degree of enhancement.

While the feedback system is stable, the degree of high frequency enhancement created by the feedback system remains relatively constant. Consequently, the ratio between the non-processed external signal and the processed internal signal remains essentially constant. However, when the system begins to destabilize, the enhancement of signals within the enhancement range increases. Thus, although the signal from external microphone 300 remains unaffected, the signal from internal microphone 28 increases, thus increasing the enhancement ratio. In the preferred embodiment, the feedback system is designed so that the degree of enhancement, and thus the enhancement ratio, is proportional to the gain. As the system approaches instability, the enhancement ratio exceeds the threshold value, indicating that instability is imminent. Comparing circuit 306 suitably generates a suitable output signal proportional to the degree of enhancement to gain control circuit 308 to reduce or increase the gain of cancellation circuit 310. As the gain is reduced, the system returns to stable operation, and the enhancement again drops below the threshold value.

Similarly, the midband frequencies within the cancellation band that are not normally subject to enhancement may be monitored for excessive cancellation. Most cancellation systems are designed to provide a certain amount of cancellation, e.g. 20 dB. If the system exceeds this threshold, it may become unstable. Alternatively, for a feedforward system, excessive cancellation actually reduces the overall effectiveness of the system by enhancing signals in the enhancement frequency ranges. Thus, the external and internal signals may be monitored to determine the degree of cancellation the system is providing. The comparing circuitry determines whether the cancellation signal is too high; if so, the gain of the system is reduced until the cancellation signal is again within the proper parameters.

If desired, a feedback cancellation system according to the present invention may additionally employ microphone 300 in a feedforward system operating in conjunction with the feedback system to reduce the high frequency enhancement caused by a high gain feedback system. It may be desirable in various applications to employ an earpiece 1 with an open back for maximum low frequency response. External microphone 300 is located at a suitable predetermined distance away from sound generator 22. Sound detected by external microphone 300 is converted into electrical signals which are provided to cancellation circuit 310. Cancellation circuit 310 then generates a cancellation signal based in part upon the detected external signal, which is provided to sound generator 22. Because the propagation speed of soundwaves and the distance between external microphone 300 and sound generator 22 are known, the propagation delay of the soundwaves between external microphone 300 and sound generator 22 may be calculated to facilitate the proper phase relationship between the noise and anti-noise. Thus, sound generator 22 generates soundwaves precisely inverted with respect to soundwaves detected by external microphone 300 propagating along a line between external microphone 300 and sound generator 22.

Feedforward systems are generally very sensitive to variations in the characteristic transfer function of the system, making them unsuitable for many applications in which the acoustic properties of the cancellation system are subject to variation. The feedforward system of the disclosed embodiment, however, cooperates with the feedback system to improve the system performance and stability. The feedback system effectively provides cancellation in the midband frequencies of the cancellation system, but as it approaches instability, the amplitude of signals in the enhancement region are enhanced. If unchecked, the enhanced frequencies eventually achieve sufficient amplitude to destabilize the system. The feedforward system, however, effectively cancels high frequency components of the incident noise within the enhancement range, thus improving the overall quality of the system.

Figure 3A:
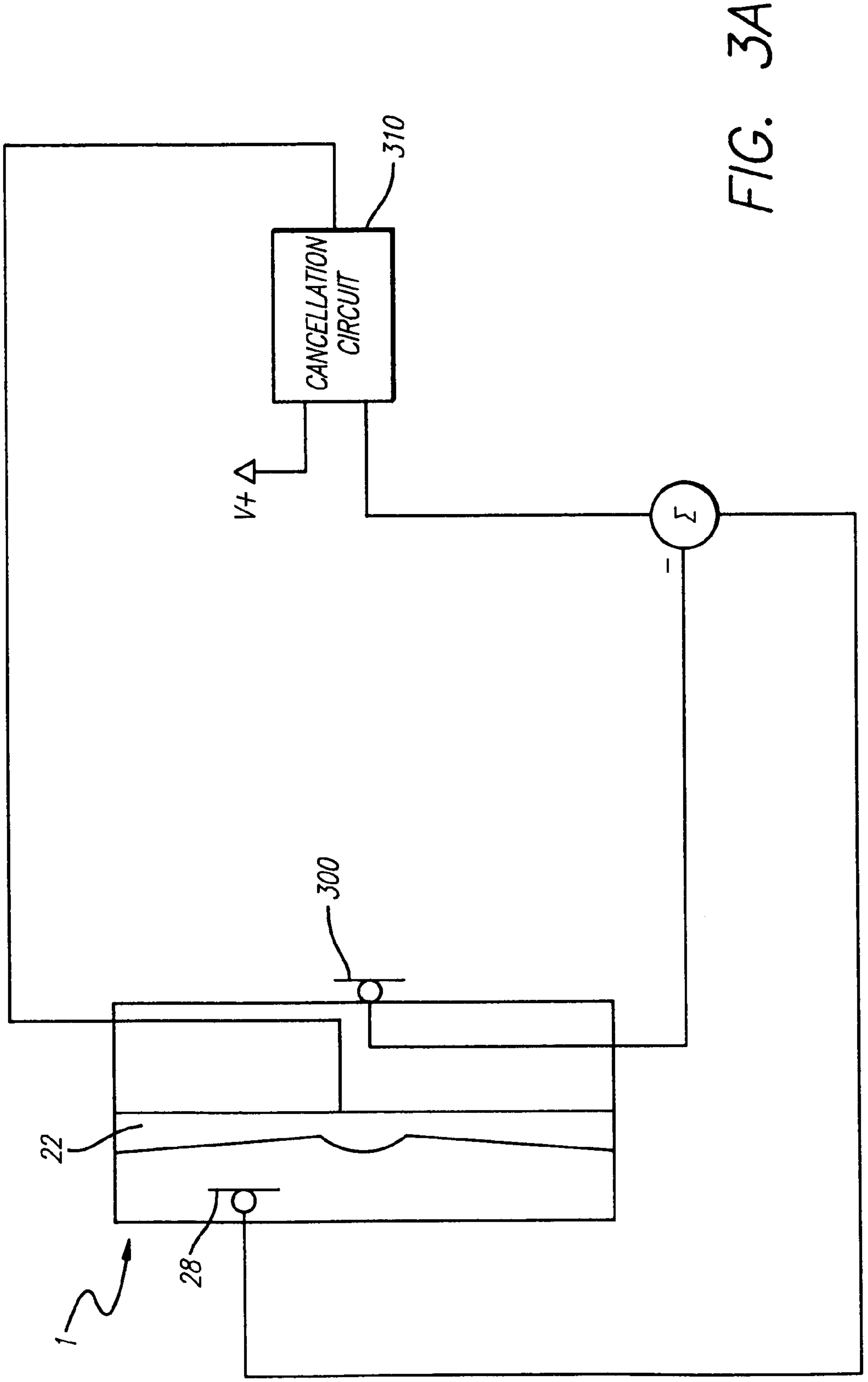

The feedforward system may also be incorporated into the feedback loop to improve cancellation in the system's cancellation band. As shown in FIG. 3A, signals generated by external microphone 300 are mixed with the residual signal generated by internal microphone 28 (as opposed to being mixed with the cancellation signal generated by cancellation circuit 310 and applied as a component of the driver signal applied to the sound generator). Because the feedforward signal is mixed with the residual signal instead of the cancellation signal, the feedforward signal is not subject to cancellation by the feedback portion of the cancellation system. The feedforward system is designed to cancel within the cancellation band, adding to the cancellation supplied by feedback system. As a result, the gain of feedback system may be reduced to a level less susceptible to instability.

In accordance with another aspect of the present invention, it is recognized that changes in the pressure of earpiece 1 against the user's head affect the acoustic properties of earpiece 1 and may cause instability. Instability can therefore be mitigated by varying the gain of the feedback loop according to the sensed pressure. To this end, when pressure is applied or released to the headset, gain may be reduced or the cancellation system disabled altogether.

Figure 4:
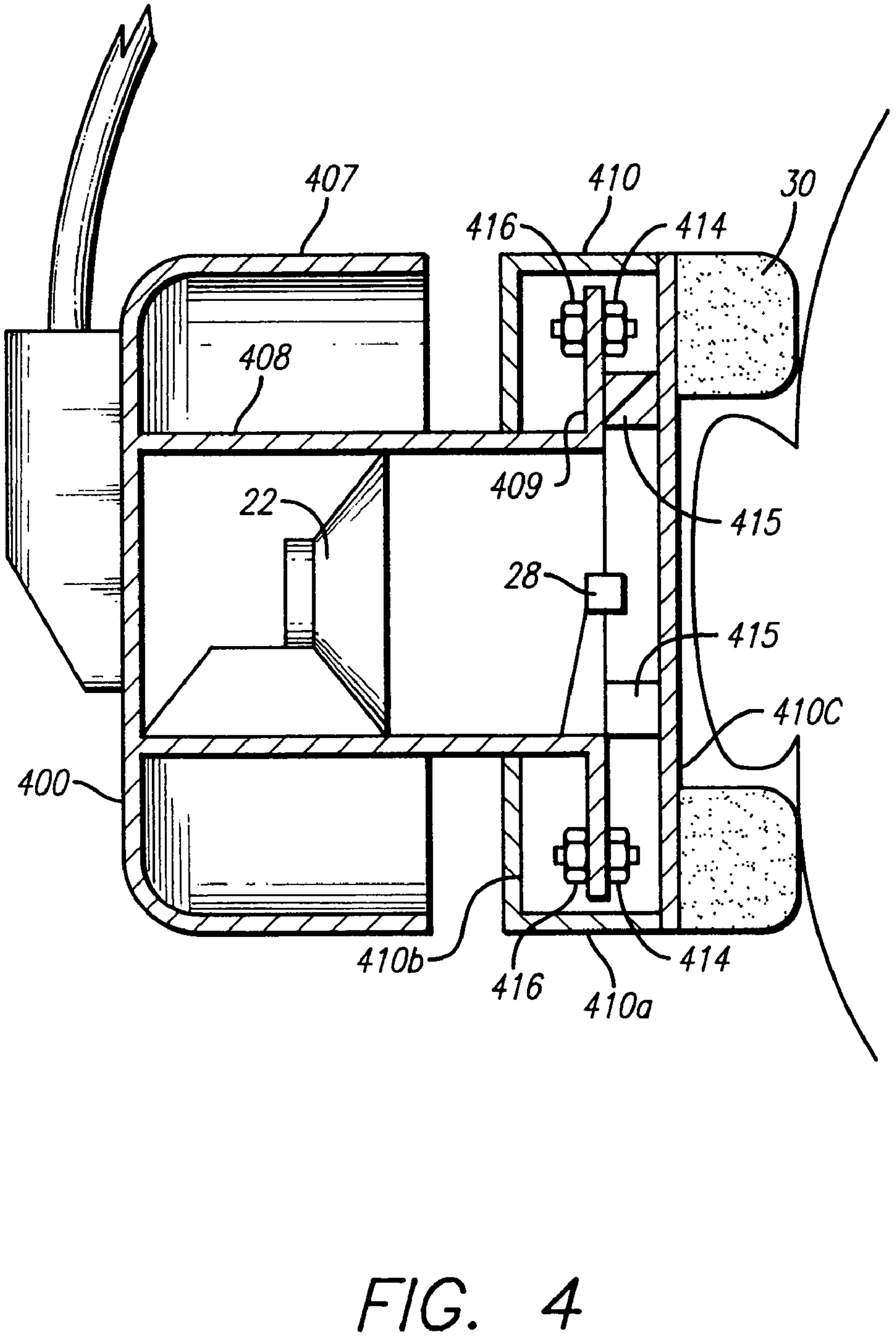
FIG. 4 is a sectional view of the headset incorporating a pressure sensitive noise cancellation system according to various aspects of the invention.

Referring to FIG. 4, an earpiece 400 incorporating this feature preferably incorporates a mechanism for sensing when the pressure of the earpiece against the user's ear is outside of a predetermined range, for example, exceeding a maximum value, or less than a minimum value. In the embodiment of FIG. 4, such an earpiece 400 comprises a first shell portion 407, a second shell portion 410, and annular foam pad 30. First shell portion 407 is generally semi-spherical or cylindrical, and concave. An annular wall 408 extends from within first shell portion 407, generally coaxial, with shell portion side wall, to a region beyond the plane of the shell portion lip. A flange 409 extends radially outwardly from the free axial extremity of annular wall 408. Second shell portion 410 comprises an annulus 410*a*, first and second flanges 410*b* and 410*c*. Annulus 410*a* suitably manifests an outer radius approximately equal to the radius of the lip of shell portion 407, and is disposed coaxially with first shell portion 407. First flange 410*b* extends radially inwardly from an axial extremity of annulus 410*a* between flange 409 and the lip of first shell portion. Second flange 410*c* extends radially inward from the other axial extremity of annulus 410*a*. Foam pad 30 is affixed coaxially to the outer surface of second flange 410*b* of the second shell portion 410.

Sound generator 22 is suitably mounted coaxially within annular wall 408 and microphone 28 is mounted on the open side of sound generator 22. First and second sets of switches 414, 416 are mounted on the respective sides of flange 409. Switches 414, 416 may be any suitable state changing switch normally closed or normally open depending upon the particular design of the cooperating circuitry. Switches 414, 416 are designed to change state upon application of a predetermined amount of pressure. In the preferred embodiment, switches 414, 416 are momentary contact membrane switches. Membrane switches are particularly suited to the disclosed embodiment because they are thin, easily assembled, and inexpensive. Switches 414, 416 in the preferred embodiment require little compression to change state, and preferably include or cooperate with circuitry to induce hysteresis and prevent switches 414, 416 from repeatedly switching state at pressures fluctuating near the threshold pressure. The hysteresis circuitry may be external or incorporated into the switches. Although shown in FIG. 4 as each including two switches, switch sets 14 and 16 may include any suitable number of switches. For example, three switches, spaced at approximately 120 degree intervals around flange 409, may be used to effectively detect pressure upon most portions of earpiece 1. Alternatively, however, a single switch may be used in each set if the headset design is particularly sensitive to pressure at a certain point or from a certain angle.

First switches 414 are mounted on flange 409, directed towards second flange 410*c* of second shell portion 410. A predetermined number, e.g. three, of elastomeric blocks 415, are affixed between flange 409 and second flange 410*c* of the second shell portion 410, preferably angularly spaced by about 120°. Second switches 416 are located on flange 409, directed towards first flange 410*b* of second shell portion 410.

The disposition of flange 409 of first shell portion 407 relative to first flange 410*b* and second flange 410*c* is a function of the pressure of the earpiece against the user's head. Switches 414 and 416 are disposed for actuation in response to contact with flanges 410*b* and 410*c* of second shell portion 410, respectively. The characteristics of elastomeric blocks 415 and the distance between flanges 410*b* and 410*c* are chosen to cause contact between switches 414 and flange 410*c* and switches 416 and flange 410*b* in a response to predetermined levels of pressure. For example, in the absence of pressure, elastomeric blocks 415 may force switches 416 into contact with flange 410*b*. When the pressure exceeds a predetermined lower threshold, compressing elastomeric blocks 415, switches 416 move out of contact with flange 410*b* (and hence assume their normal condition). When the pressure exceeds a predetermined upper threshold sufficient to compress elastomeric blocks 415 by a predetermined amount, switches 414 come into contact with flange 410*c* and are actuated.

If desired, switches 414 and 416 may be employed to deactivate controller 6 if the pressure of the earpiece against the user's head is outside of a predetermined range, so that controller 6 is deactivated when the pressure is less than a predetermined minimum value, e.g. when the earpieces are not being worn, or when the pressure exceeds a predetermined level, rendering the system susceptible to oscillations.

Figure 5:
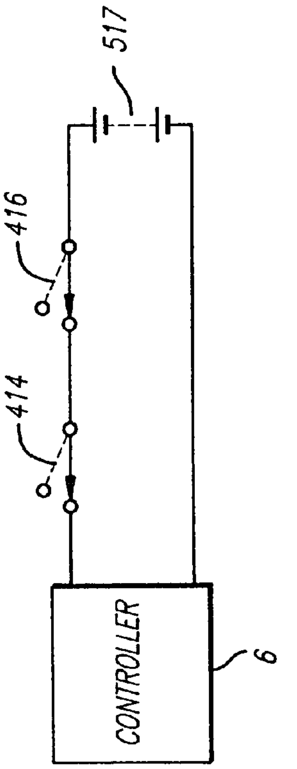
FIG. 5 is a schematic diagram of a switching system according to various aspects of the present invention.

Referring to FIG. 5, such an embodiment may be implemented employing normally closed switches 414 and 416 serially interposed between controller 6 and its power source. Controller 6 is suitably supplied with power from a battery 517. The current path from the positive terminal of battery 517 to controller 6 passes through the normally closed first and second switches 414, 416. Only single first and second switches 414, 416 are shown in FIG. 5 for clarity. In the exemplary embodiment, all of the switches are in a series configuration with each other.

Referring to FIGS. 1, 4 and 5, before earpiece 1 is placed against the user's head, elastomeric blocks 415 force second shell portion 410 away from first shell portion 407. This causes first flange 410*b* of second shell portion 410 to contact second switches 416 causing them to be open. When one of second switches 416 is open, current cannot flow to controller 6 from battery 517.

When a user puts on headset 100, first earpiece 1 is pressed against the user's head by the resilience of headband 3. The force applied by headband 3 to first shell portion 407 causes elastomeric blocks 415 to be compressed between first and second shell portions 407, 410. As elastomeric blocks 415 are compressed, first flange 410*b* of second shell portion 410 moves away from second switches 416, allowing them to close. At this point, both first and second switches 414, 416 are closed, allowing the supply of current flow from battery 517 to controller 6. Controller 6 then drives sound generator 22 to effect noise cancellation at the user's ear.

If, for some reason, an additional force is applied to force earpiece 1 towards the user's head, elastomeric blocks 415 are further compressed and first switches 414 are caused to open by coming into contact with second flange 410*c* of second shell portion 410. The opening of any one of first switches 414 interrupts the flow of current from battery 517 to controller 6, deactivating controller 6. Since controller 6 has been deactivated, the feedback loop is unable to go into oscillation so that the risk of damage to the user's ear is avoided.

Figure 6:
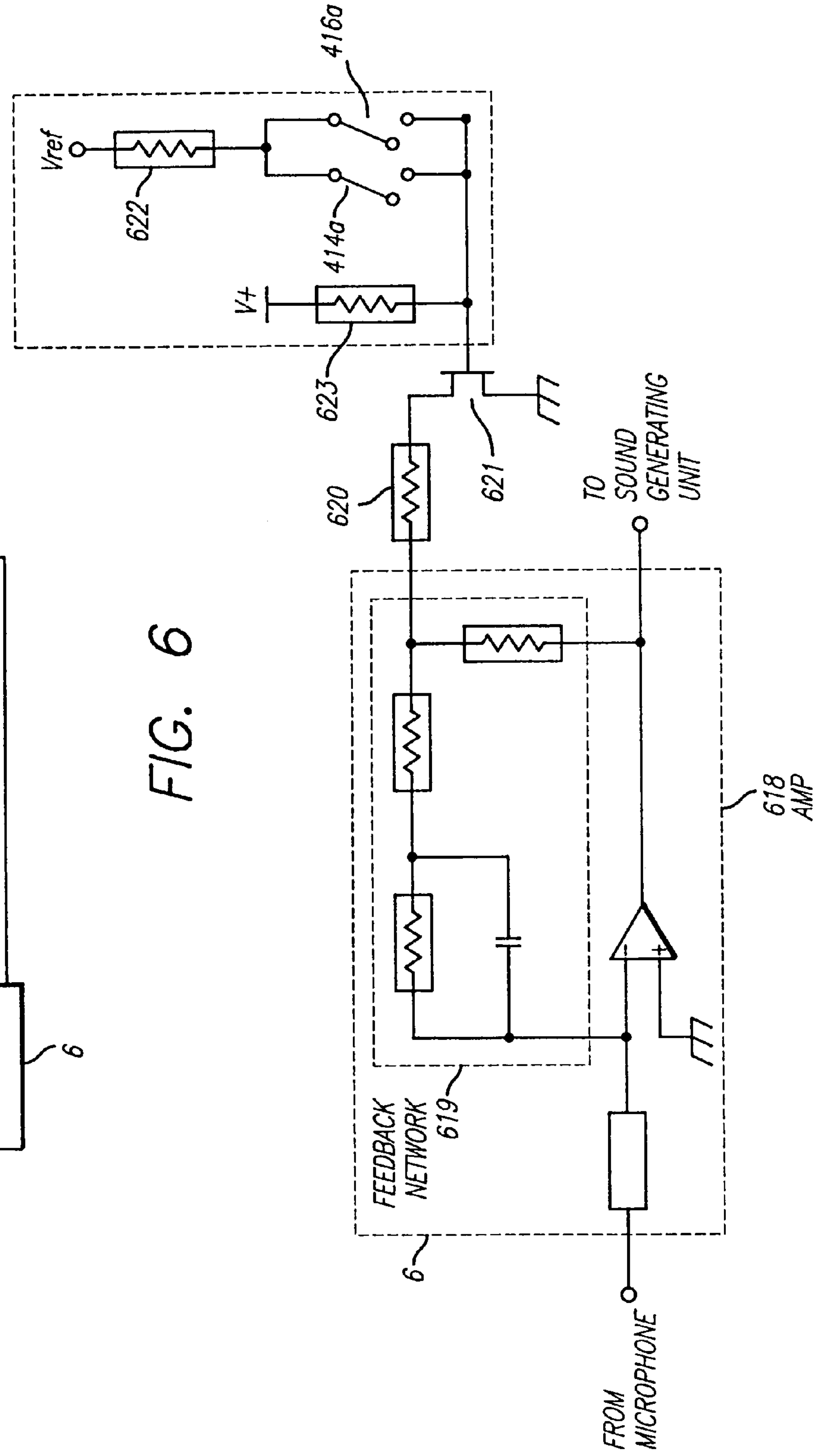
FIG. 6 is a schematic of diagram of a pressure sensitive noise cancellation control system according to various aspects of the present invention.

As an alternative to deactivating controller 6, the gain of the feedback loop may be varied in accordance with the actuation of switches 414 and 416 to preclude oscillation. Referring to FIG. 6, a suitable circuit using normally open switches 414*a* and 416*a* for effecting such gain control comprises an amplifier 618, including a feedback network, respective resistors 620, 622 and 623, and a field effect transistor (FET) 621. Amplifier 618 is provided in the feedback path of controller 6. The gain of amplifier 618 is set by feedback network 619. Resistor 620 is selectively coupled into feedback network 619, in accordance with the state of switches 414*a* and 416*a*, to selectively vary the gain of amplifier 618. Resistor 620 is coupled between a node of feedback network 619 and the drain of FET 621. Switches 414*a* and 416*a* are included in the biasing circuit of FET 621. In this embodiment, first and second switches 414*a*, 416*a* are normally open, momentary contact switches, suitably membrane switches. FET 621 is selectively rendered conductive or non-conductive accordingly to the state of switches 414*a* and 416*a*. The source of FET 621' is connected to a reference ground potential. Each switch of first and second sets of switches 414*a* and 416*a* (only one of each shown for simplicity) are connected in parallel between one terminal of resistor 622 and gate of FET 621. The other terminal of resistor 622 is coupled to a reference voltage rail $V_{ref}$ which is negative with respect to the reference ground potential. The gate of FET 621 is also coupled to a positive supply rail +V via resistor 622.

Referring to FIGS. 4 and 6, before a user puts on headset 100, second switches 416*a* are closed. This causes the potential at the gate of FET 621 to be reduced, turning off FET 621 and thereby reducing the gain of amplifier 618. Under normal wearing conditions, first and second switches 414*a*, 416*a* are both open, FET 621 is turned on and the gain of amplifier 618 is set by the feedback network 619. If an additional force is applied to earpiece 1, first switches 416 close, turning off FET 621 and thereby reducing the gain of amplifier 618 by effectively removing resistor 620 from feedback network 619. The reduction in the gain of amplifier 618 ensures that stability is maintained regardless of the transfer function of the acoustic component of the feedback loop.

Alternatively, the embodiments shown in FIGS. 5 and 6 may be combined. For instance, second switches 416 may cut the supply of current to controller 6 when headset 100 is removed. First switches 414*a*, on the other hand, as in FIG. 6, may reduce the gain of amplifier 618 when earpiece 1 is pressed too tightly to the user's head, but continue to supply power to headset 100.

Figure 7:
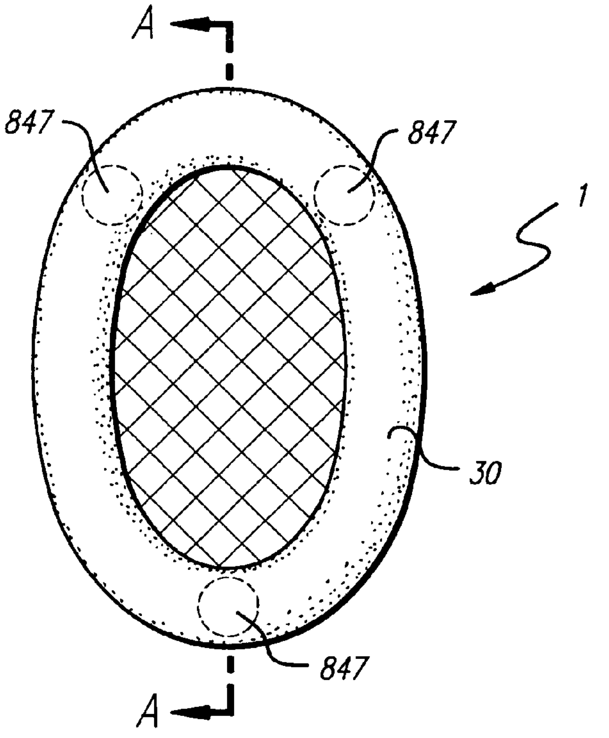
FIGS. 7 and 8 depict front and sectional side views, respectively, of a switched headset according to various aspects of the present invention.
Figure 8:
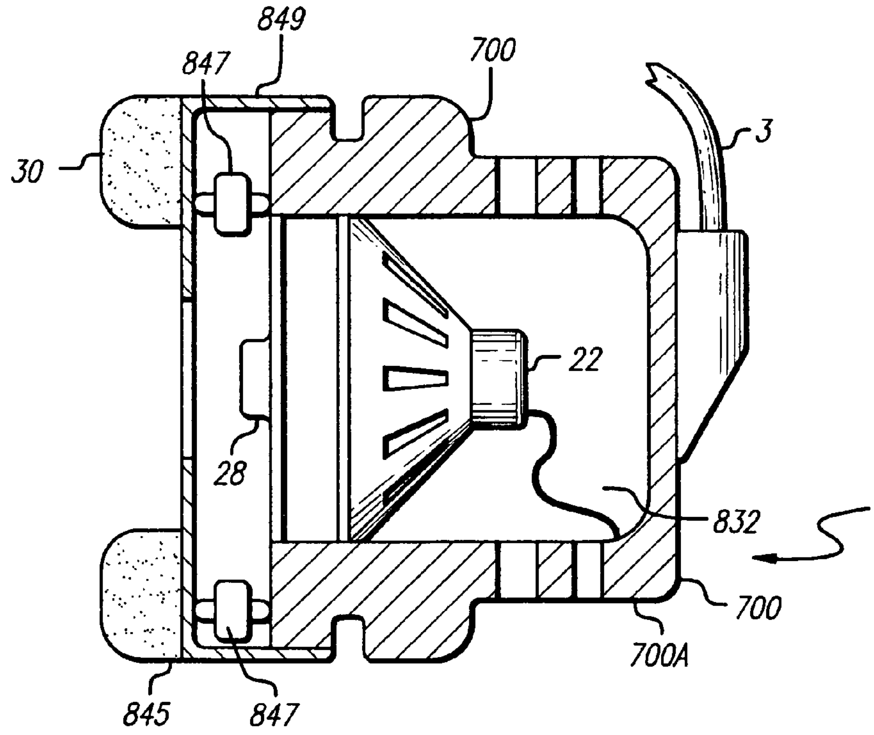

The gain of the feedback loop may also be varied as a function of the pressure of earpiece 1 against the user's head. For example, suitable pressure transducers, such as an element having a resistance which varies according to pressure or other pressure sensitive element, may be used to affect the gain of the headset circuit according to the force applied to earpiece 1 against the user's head. Referring to FIGS. 7 and 8, an earpiece 1 employing resistive pressure transducers comprises a shell 700, sound generator 22, microphone 28, an annular plate 845, pressure transducers 847, and annular foam pad 30. Shell 700 supports sound generator 22 coaxially within a central chamber 832 formed by shell 700. If desired, shell 700 may include a transverse sidewall 700*a*, inset from the outer periphery of the shell (e.g., adjacent pad 30). Apertures communicating with chamber 832 to the rear of sound generator 22 may be formed through transverse wall 700*a* to enhance the low frequency response of the earpiece 1. As previously noted, disposition of the passageways in the sidewall reduces susceptibility to blockage.

Chamber 832 is open at the earside of shell 700. Microphone 28 is supported at the open end of chamber 832. Annular plate 845 is located coaxially with shell 700 and separated from shell 700 by a predetermined number, e.g. three, resistance pressure transducers 847, preferably disposed with equal angular spacing about plate 845, e.g. separated by 120°. Transducers 847 are electrically connected in series. Any numbers of transducers may be used, although three are shown in FIG. 7. An annular seal 849 forms a circumferential wall to the chamber defined between annular plate 845 and shell 700. Annular foam pad 30 is affixed coaxially to the outer face of annular plate 845.

Referring to FIG. 9*a*, an embodiment of a circuit according to the present invention is shown in which the gain of controller 6 may adjust according to the force exerted on earpiece 1 by, e.g. the user's head. Suitably, a voltage divider is formed by pressure transducers 947 connected in series with a resistor 950. The output from the voltage divider is suitably amplified by an inverting amplifier 951, the output of which is applied to the gate of FET 621. The voltage existing at the voltage divider is proportional to the pressure exerted upon pressure transducers 947. As the pressure upon pressure transducers 947 increases, the gate voltage for FET 621 decreases, reducing the conductivity of FET 621 and accordingly reducing the gain or of feedback amplifier 618.

Alternatively, where feedback amplifier 618 includes multiple stages, the coefficients of filters included in feedback amplifier 618 may be varied as the pressure increases to maintain the frequency response of the cancellation system loop. Varying the filter coefficients of the cancellation system preserves the stability of the system and maintains the bandwidth. Thus, increased pressure of earpiece 1 upon the user's head varies the gain and/or frequency response of the cancellation system to avoid instability.

A similar gain control system applied to a feedforward system enhances the cancellation system's effectiveness. When pressure is sensed upon earpiece 1, the coefficients of the filters are adjusted to vary the gain, frequency response, and phase of the feedforward cancellation signal. With proper calibration, the proper amplitude and phase relationship of the cancellation signal to the primary signal may be maintained.

In a further embodiment, controller 6 may be deactivated when the pressure of earpiece 1 against the user's head falls below a predetermined threshold. Referring to FIG. 9*b*, the output from the voltage divider circuit and amplifier 951 may be suitably applied to the input of a suitable threshold comparator circuit, such as a Schmitt trigger circuit 952. The power supply is permanently connected to amplifier 951, Schmitt trigger 952 and the voltage divider to provide continuous power. The output of the Schmitt trigger circuit 952 is connected to the base of a switching transistor 953 connected in series with battery 517 and controller 6. When the output of the pressure-varying voltage divider and amplifier 951 falls below a lower threshold voltage of Schmitt trigger 952, transistor 953 turns off, opening the circuit connecting controller 6 to battery 517. Consequently, the cancellation system is turned off until the pressure on transducers 947, and correspondingly the voltage provided to the Schmitt trigger, increases enough to switch the output of Schmitt trigger 952 on and reconnect battery 517 to controller 6.

A wide range of other techniques for measuring the pressure of earpiece 1 against the user's head may also be employed. For example, a subsonic acoustic signal may be employed to determine the current acoustic properties of the earpiece. Referring to FIG. 10, a sound generating unit 22 and a microphone 28 are mounted within an earpiece 1. A feedback loop is formed between microphone 28 and sound generating unit 22 through a cancellation circuit 310. A summing circuit 1065 adds the output of a subsonic frequency signal generator 1066 to the output of cancellation circuit 310. The subsonic component of the output of sound generating unit 22 is, of course, outside of the normal human audible range and is thus inaudible to a person using earpiece 1. However, the subsonic acoustic signal, generated within earpiece 1, is detected by microphone 28. The level of the subsonic acoustic signal detected by microphone 28 is dependent upon the acoustic properties of the earpiece 1, which are affected by the pressure between earpiece 1 and the user's head.

The subsonic signal may be mixed with the cancellation signal generated by cancellation circuit 310 in a feedforward configuration so that the subsonic signal remains at a constant level regardless of the gain of the system. This level may be set for the particular cancellation system so that cancellation circuit provides the same level of cancellation regardless of the individual characteristics of sound generator 22, microphone 28 and the other system components. This arangement has particular application to systems in which sound generator 22 and microphone 28 are interchangeable with others, such as airplane headsets. Alternatively, subsonic signal may be mixed with the residual signal generated by microphone 28, so that the amplitude of the subsonic signal is modulated by the gain of the system. This forms a feedback loop in which the system continuously adjusts the gain to maintain the subsonic signal at a particular level.

The output of microphone 28 is passed through a low pass filter 1068 to a suitable level detecting circuit 1069, e.g. a rectifying and smoothing circuit. Alternatively, filter 1068 may be a bandpass filter having an appropriate center frequency and quality. Subsonic frequency signals are transmitted by filter 1068, and the gain or frequency response of cancellation circuit 310 is adjusted according to the output of level detecting circuit 1069, which varies according to the pressure of earpiece 1 against the user's head. Similarly, level detecting circuit 1069 may replace the gain control switch circuit in FIG. 6, the output of level detecting circuit would be amplified and applied to the gate of FET 621. Like the switch circuit of FIG. 6, the output of level detecting circuit 1069 reduces amplifier's 618 gain by turning FET 621 on when sufficient pressure is exerted upon earpiece 1. Alternatively, the output of level detecting circuit 1069 may vary the frequency response of the cancellation system according to the pressure exerted on earpiece 1. Similarly, the output of level detector 1069 may be used to determine when headset 100 has been removed from the user's head.

Alternatively, the gain of the cancellation system may be controlled by detecting particular signals that are commonly generated when abnormal pressure on earpiece 1 causes the cancellation system to become unstable or less effective. As previously noted, when the cancellation system becomes unstable, it typically generates low frequency (drone) and high frequency (squeal) oscillations. The onset of drone and/or squeal signals may be detected and employed to reduce gain and control instability. Although drone and squeal signals do not normally occur in feedforward systems, a similar detection and gain control system may be used to control inadvertent feedback caused by loss of isolation of external feedforward microphone 300 from sound generator 22.

Referring now to FIG. 11, an exemplary circuit 1100 for controlling system gain in accordance with sensed drone or squeal signals suitably comprises respective bandpass filters 1174 and 1175, a summing circuit 1176, a rectifying circuit 1178, respective resistor 1179 and 1181, a capacitor 1180, and a field effect transistor (FET) 1182. Circuit 1100 cooperates with microphone 28 in earpiece 1, and FET 621 in the circuit of FIG. 6. The output from microphone 28 in earpiece 1 is applied to cancellation circuit 310 (not shown) and to bandpass filters 1171 and 1175. Bandpass filters 1171 and 1175 are tuned to the above-mentioned drone and squeal frequencies, respectively. If desired, control for both earpieces may be effected using a single set of filters 1174, 1175. The output from the microphone 28 in another earpiece may also be applied to the filters 1174, 1175 and the output of the rectifying circuit 1178 applied to gain control elements for both earpieces. The outputs of filters 1174, 1175 are provided to summing circuit 1176, the output of which is provided to rectifying circuit 1178, and the rectified signal is then provided to the gate of a field effect transistor (FET) 1182 via a resistor 1179. The gate of FET 1182 is also coupled to reference ground potential via the parallel combination of capacitor 1180 and resistor 1181. The drain of FET 1182 is coupled to the gate of FET 621 of the circuit shown in FIG. 6.

Preferably, the headset system is designed so that the drone and squeal frequencies are outside its noise canceling bandwidth. Therefore, under normal operating conditions, the output of microphone 28 contains very little power at the drone and squeal frequencies. Consequently, under normal conditions the outputs of filters 1174, 1175 are very low, and only a small voltage is applied to the gate of FET 1182. The minimal voltage applied to FET 1182 is too low to turn it on significantly and the gain of the feedback system is maintained.

If, however, earpiece 1 is pressed against the user's head with abnormal force, the feedback system may begin to oscillate at either or both of the drone and squeal frequencies. Under these circumstances, the output from summing circuit 1178 becomes significant. Capacitor 1180 charges up to a level set by a voltage divider formed by resistors 1178, 1181 and the output voltage of rectifying circuit 1178. The charging time constant of capacitor 1180 is determined by the values of capacitor 1180 and resistors 1179, 1181.

As capacitor 1180 charges, FET 1182 is turned on, turning off FET 621 and reducing the gain of the feedback system. As the gain of the system is reduced, the oscillations diminish as it becomes stable again. Once the system has become stable, the output from summing circuit 1176 again becomes insignificant. Capacitor 1180 then discharges through resistor 1181, thereby increasing the gain of the system.

If it is assumed that the instability of the system is the result of a short term event, the resistance of resistor 1181 is chosen to be relatively large so that the time constant of the capacitor 1180 and resistor 1181 circuit is at a few seconds. Thus, when the gain of the system has returned to its original value, the event causing the instability has passed. If the event continues for a longer period, the user may experience mild and harmless short bursts of drone and squeal as the system restarts to oscillate, before the gain of the system is again reduced.

The values of capacitor 80 and resistors 1179, 1181 may be suitably chosen so that FET 1182 is turned off quickly (short attack time), but is turned on relatively slowly (long release time). In such case, resistor 1179 will have a relatively low resistance to provide a short attack time, and resistor 1181 a relatively high resistance to provide a longer release time. This arrangement cuts off unpleasant squeals almost as soon as they begin. The slow release to operation prevents recurrence of the of the squeal immediately after it is eliminated. In the preferred embodiment, the attack time is about 0.2 seconds, and the release time is 1 or 2 seconds. Alternatively, if the system is fairly stable, a longer attack time may be provided, allowing a short burst of squeal or drone to heard by the user to indicate that the system is becoming unstable.

Alternative mechanisms for detecting the squeal and drone may also be employed. For example, a circuit 1200 employing phase lock loop (PLL) circuits to detect the signals is shown in FIG. 12. Circuit 1200 suitably includes respective PLL circuits 1294 and 1295, a two input OR gate 1296, a latch circuit 1297, a transistor 1202 and resistor 1294. The output from microphone 28 in earpiece 1 is applied to cancellation circuit 310 (not shown) and to the inputs of PLL circuits 1294, 1295. PLL circuits 1294, 1295 may be implemented using integrated circuits, such as the LM565 PLL, manufactured by National Semiconductor. The capture range of first PLL circuit 1294 is arranged to correspond to the drone frequency range and that of second PLL circuit 1295 to the squeal frequency range. The lock detect (LOCK) outputs of PLL circuits 1294, 1295 are applied to the inputs of two-input OR gate 1296, the output of which is applied to the input of latch circuit 1297. Latch circuit 1297 may be reset by means of a user operable switch 1298. The output of latch circuit 1297 is coupled to the base of transistor 1202 via a resistor 1299. The collector of transistor 1202 is coupled to the gate of FET 621 of the circuit in FIG. 6.

Under normal operating conditions, the level of the signals output by microphone 28 at the drone and squeal frequencies are too low to allow the PLL circuits 1294, 1295 to lock and, in its initial condition, the output Q of the latch circuit 1297 is at logic low. Thus, transistor 1202 is turned off, FET 621 is turned on, and the system gain is at its maximum.

If, however, the feedback system begins to oscillate, the drone or squeal frequency is detected by PLL circuits 1294, 1295. When this happens, one or both of the LOCK outputs of PLL circuits 1294, 1295 changes to logic high. The output of OR gate 1296 responds by going to logic high, causing a logic high signal to be asserted at the output of latch circuit 1297. The logic high output of latch circuit 1297 causes transistor 1202 to turn on, which turns off FET 621, thus reducing the gain of the feedback system.

When normal conditions are reestablished, the system is again stable and the output of OR gate 1296 returns to logic low. However, FET 621 remains off due to latch circuit 1297 continuing to assert a logic low signal. Full gain is reestablished by the user toggling a reset switch 1298, which sets the output of latching circuit 1297 to logic low. If switch 1298 is toggled before the abnormal conditions have ended, the gain of the system is again reduced when PLL circuits 1294, 1295 detects oscillation by the feedback system.

In accordance with another aspect of the present invention, power conservation mechanisms can be incorporated into the noise cancellation system. As previously noted, pressure on the earpieces can be sensed, and power removed from all or part of the circuitry when the headset is not being worn by the user. In addition, the system gain can be reduced or power removed from all or part of the circuitry, in accordance with the level of ambient (external) noise, e.g. when ambient is not at a level that requires active cancellation. For example, referring to FIG. 13, controller 6 may include suitable power control circuitry 1300 interposed between the power source, e.g. battery 517, and the remainder of the controller circuitry, for conversion reference generally denominated herein as cancellation circuitry 310. Power control circuitry 1300 may be configured in series with switches 414, 414*a*, 416, 416*a* of FIGS. 5 and 6. Power control circuitry 1300 selectively applies power to cancellation circuitry 310, in accordance with the level of signals sensed by an external microphone, e.g., microphone 300 (FIG. 3). Circuit 1300 suitably comprises a switching transistor 1307, a rectifying and switching circuit 1308, and a voltage comparator 1310, e.g., differential amplifier. Rectifying and smoothing circuit 1308 is coupled to an external microphone, e.g., suitably microphone 300 (FIG. 3). If desired, a low pass or bandpass filter (not shown) may suitably be located between microphone 300 and rectifying and smoothing circuit 1308 to attenuate irrelevant or inaudible soundwaves. The output of rectifying and smoothing circuit 1308 is coupled to an input of comparator 1310, suitably a differential amplifier. The other input of comparator 1310 is supplied with a reference voltage $V_{ref}$. The output of comparator 1310 drives switching transistor 1307. Comparator 1310 and rectifying and smoothing circuit 1308 are continuously connected to battery 517, regardless of the state of switching transistor 1307.

During normal operation in a high noise environment, external microphone 1309 generates a high amplitude signal, which is rectified and smoothed by rectifying and smoothing circuit 1308. Comparator 1310 compares voltage generated by rectifying and smoothing circuit 1308 with the reference voltage $V_{ref}$. $V_{ref}$ is preset at a voltage suitably representative of the loudness level above which cancellation is desired. If desired, $V_{ref}$ may be adjusted by the user to suit hearing and power conservation needs. While the headset is operating in an environment louder than the preset threshold, the output from rectifying and smoothing circuit 1308 is greater than reference voltage $V_{ref}$, and comparator 1310 provides a high signal to the base of switching transistor 1307, turning it on and connecting the supply of current to cancellation circuit 310.

If, however, the environmental noise level and the corresponding microphone output drop below the reference voltage, the output from rectifying and smoothing circuit 1308 falls below reference voltage $V_{ref}$. Comparator 1310 drives the signal provided to the base of switching transistor 1307 low, turning transistor 1307 off and cutting the power supply to cancellation circuit 310. Hence, cancellation circuit 310 only operates when ambient noise exceeds a predetermined threshold. Because considerably less power is consumed in environments having low or varying noise levels, the service life of battery 517 is extended.

In an alternative embodiment, the power supply to the controller is not interrupted, but voltage supplied to portions of the controller circuitry, such as the power amplifier or the equalizer, is adjusted according to the noise level so that the circuity is supplied with only as much power as it requires. Referring now to FIG. 14, such a system can advantageously be implemented employing a controller 6 having a feedback portion comprising a variable bandwidth low pass filter 1415, and amplifier 1416, cooperating with internal microphone 28, rectifying and smoothing circuit 1417 and a switch mode voltage regulator 1418. Electrical signals from microphone 28 (mounted within earpiece 1 (not shown)) are applied to filter 1415. The output of low pass filter 1415 is coupled to an input of an amplifier 1416. The output of amplifier 1416 drives sound generator 22 (FIG. 3) in earpiece 1. Although shown in FIG. 14 as a single unit, in practice amplifier 1416 may be implemented with multiple stages of separate amplifiers. The output of amplifier 1416 is also provided to the input of rectifying and smoothing circuit 1417. The output of rectifying and smoothing circuit 1417 controls the bandwidth of low pass filter 1415, and is also provided to voltage regulator 1418 which receives current from battery 517.

Sound detected by microphone 28 is converted to electrical signals, which are transmitted through low pass filter 1415 to amplifier 1416. The amplitude of the output of amplifier 1416 indicates the level of unwanted noise. The output from amplifier 1416 is suitably rectified and smoothed by rectifying and smoothing circuit 1417 to produce a suitable corresponding control voltage, which is provided to switch mode voltage regulator 1418. Voltage regulator 1418 varies its output voltage, which is supplied to amplifier 1416, according to the current amplitude of the detected noise level. Thus, when the amplitude of the noise to be canceled is low, a low power supply voltage is supplied to amplifier 1416. However, if the amplitude of the noise to be canceled is high, switch mode voltage regulator 1418 increases the power supply to amplifier 1416 enough to generate the proper waveform.

When the noise level is low, reducing the supply voltage to amplifier 1416 may result in the noise canceling feedback system becoming unstable, especially if the controller is of the virtual earth type. Instability is avoided in the embodiment of FIG. 14 by variable bandwidth low pass filter 1415. As the amplitude of the noise to be canceled decreases, causing a corresponding reduction in the power supply voltage to amplifier 1416, the bandwidth of low pass filter 1415 is reduced in accordance with the signal from rectifying and smoothing circuit 1417. Reducing the bandwidth of the signal provided to amplifier 16 diminishes the feedback system's tendency towards instability.

Referring to FIG. 15, switch mode voltage generator 1418 suitably comprises a dedicated integrated circuit (IC) 1519, such as the Linear Technology LT1108, cooperating with respective resistors 1520, 1521, 1523 and a transistor 1529. Resistor 1520 and resistor 1521 form a potential divider connected between the output of regulator 1418 and ground. The voltage at the node between resistors 1520 and 1521 is applied to integrated circuit 1519 where it is compared with an internal reference voltage. The result of the comparison is used to adjust the switching of the input current supply to thereby control the output voltage.

Transistor 1529 is employed in cooperation with the voltage divider, to effect variation of the voltage applied to IC 1519, and hence the output voltage, in accordance with the output of rectifier and smoothing circuit 1417. Transistor 1529 is connected with collector coupled to the node between resistors 1520 and resistor 1521, emitter is coupled to ground through a resistor 1523, and base receptive of the output of rectifying and smoothing circuit 1417. As the output from rectifying and smoothing circuit 1417 increases with increasing amplitude of the noise to be canceled, transistor 1529 is progressively turned on, forming a current path parallel to resistor 1521. This has the effect of reducing the voltage of the node between resistor 1520 and resistor 1521. This voltage is compared by integrated circuit 1519 with the internal reference voltage, and the input current switching is suitably adjusted to increase the output voltage. Thus, an increase of detected noise increases the output signal of rectifying and smoothing circuit 1417, which results in a corresponding increase in the supply voltage produced by voltage regulator 1418.

As an alternative, current control circuitry may be integrated into the power amplifier, thus obviating the necessity of switching regulator 1418 to vary the voltage supplied to amplifier 1416. A power amplifier drawing a variable current reduces the number of components in the system. For example, amplifier 1416 may comprise a suitable power amplifier or other suitable signal amplifier which varies bias conditions in accordance with the amplitude of the noise to be canceled. Referring to FIG. 16, an example of such a suitable power amplifier comprises a long-tailed pair input stage 1640, a complementary output stage 1641 and a driver stage 1642. The bias currents for the long-tailed pair 1640 and output stage 1641 are set by a current source 1643.

Driver stage 1642 comprises a transistor 1644, the emitter of which is connected to ground and the collector of which is connected to the base of a PNP transistor 1662 of output stage 1641. The collector of transistor 1644 is also connected to a level shifter 1645 comprising two diodes 1646, 1647 and a resistor 1648 in series. The other end of level shifter 1645 is coupled to the base of an NPN transistor 1663 of output stage 1641. Resistor 1648 acts to set the bias currents of output stage 1641, i.e. the base currents of transistors 1663, 1662 are set by the voltage across resistor 1648 which is itself dependent on the current flowing therethrough.

Current source 1643 comprises a PNP transistor 1650, which together with a resistor 1651 forms the tail of long-tailed pair 1640, and a PNP transistor 1652, having collector connected to the base of NPN transistor 1663 of output stage 1641 and emitter connected to a supply rail $V_{cc}$ via a resistor 1653. The bases of transistors 1650, 1652 are coupled together. A resistor 1656 and a capacitor 1655 are connected in parallel between the bases of transistors 1650, 1652 and supply rail $V_{cc}$.

The output of the amplifier is applied to a rectifying circuit 1660. The output of rectifying circuit 1660 is applied to the base of a transistor 1661. The emitter of transistor 1661 is connected to ground via a resistor 1664 and its collector is coupled to the bases of transistors 1650, 1652.

In use, the current demand of the amplifier is set by the voltage applied to the bases of transistors 1650, 1652, which is in turn controlled by as controlled by transistor 1661 setting current flowing through resistor 1648. As the output amplitude of the amplifier increases according to increasing amplitude of the noise to be canceled, transistor 1661 is progressively turned further on thereby increasing the collector currents of transistors 1650, 1652. When the amplitude of the output of the amplifier decreases, transistor 1661 is progressively turned off, thereby reducing the collector currents of transistors 1650, 1652. As the collector current of transistor 1652 varies, the biasing of output stage transistors 1662, 1663 changes, thereby altering the quiescent current of the amplifier and hence the current demand of the controller. Capacitor 1655 and resistor 1656 ensure that current source 1643 responds to the envelope of the output of the amplifier instead of its instantaneous value.

If desired, headset 100 may be further equipped with an audio input system for providing desired acoustic signals (pass through signals), like music or speech, to the user while maintaining cancellation of undesired noise. In accordance with another aspect of the present invention, a proper balance of high frequency and low frequency signals is maintained by employing an input system which mixes the pass through signals with both the residual signal provided to controller 6, and, in addition, with the cancellation signal provided to sound generator 22. Mixing the input signal with both the residual signal and the cancellation signal permits balanced sound in spite of the high frequency rolloff of controller 6 and cancellation by the cancellation system. As shown in FIG. 17, the desired input signal (pass through) is provided to a summing amplifier 1700 which also receives the signal generated by internal microphone 28 in earpiece 1. The output of summing amplifier 1700 is provided to cancellation circuit 310. Where, as in the embodiment of FIG. 17, the noise cancellation system is at least in part a feedback system, the bandwidth of the noise cancellation is limited to maintain stability; a high frequency rolloff significantly attenuates signals above a cutoff frequency. Thus, the response of the cancellation system diminishes rapidly for high frequencies, while low frequencies remain essentially unaffected.

The same input (pass through) signal is also applied to a second summing amplifier 1702, which mixes the input signal with the output of cancellation circuit 310 for application to sound generator 22. Thus, the input signal is input to the cancellation system after the cancellation signal is generated, as well as before the residual signal (from microphone 28) is processed. The addition of the input signal to the cancellation signal restores the high frequencies that are attenuated by the cancellation circuitry. The low frequency portion of the input signal provided to second summing amplifier 1702, however, is subject to cancellation by the cancellation system because, unlike high frequency signals, the low frequencies are within the cancellation bandwidth of the noise cancellation system. Thus, the high frequencies are effectively transmitted to the listener, while low frequencies are canceled by the cancellation system. In sum, the input signal is mixed with the cancellation signal twice; the cancellation system cancels half of the low frequency signals and filters out half of the high frequency signals. As a result, the overall remaining input signal is a relatively balanced signal which includes proper levels of both high and low frequencies. Although some equalization or filtration may be required, significantly reduced adjustments are required to generate the proper pass through signal. Instead, the sensitivities of the sound generator 22, the cancellation circuit 310, and the internal microphone 28 are simply balanced to provide the proper amplitude for the input signal. In addition, the phase relationships of the resulting signals may be adjusted to provide the proper balance.

A controller in accordance with the present invention may include various combinations of the features described herein, e.g. one, a plurality, or all. For example, as shown in FIG. 18, an exemplary controller 1801 adapted for use with a two earpiece headset may include various of a pressure sensing system based on a subsonic acoustic signal similar to that shown in FIG. 10, power saving circuitry similar to that shown in FIG. 5, and an audio input pass through system similar to that shown in FIG. 17. Controller 1801 suitably comprises: an input signal (comms) equalizer 1800; respective right and left channels, each comprising a mixer 1802R, 1802L, a low pass filter 1804R, 1804L, an equalizer 1808R, 1808L, a muting circuit 1810R, 1810L, a voltage controller 1814R, 1814L, and a power amplifier 1806R, 1806L; an oscillator 1812; an error amplifier 1816; a buffer (not shown); and a level shifter 1818.

Input signal (comms) equalizer 1800 may comprise any suitable circuit which receives a pass through input signal that the user is to hear and separates it into two separate channels (left and right). Comms equalizer 1800 further amplifies the input signal to provide a suitable signal to the cancellation system. Comms equalizer 1800 suitably includes a volume control for each channel, substantially identical, one for each earpiece.

Each of the right and left pass through signals from comms equalizer 1800 is provided to both an associated mixer 1802 and power amplifier 1806. Mixers 1802 (generally corresponding to mixer 1700 of FIG. 17), mix the input signal received from comms equalizer 1800 with the residual signals received from earpiece microphones 27, 28 and from the opposite mixer 1802. Power amplifiers 1806, mix the pass through input signals with the cancellation signals and a low frequency, e.g. 10 Hz, signal from oscillator 1812. This circuit arrangement corresponds to the audio play through system of FIG. 17 in which the input signal is mixed with the residual signal received from microphones 27, 28 and is also mixed with the cancellation signal generated by the system and provided to sound generator 22.

An exemplary circuit for right mixer 1802R and left lowpass filter 1804L is shown in FIG. 19. Left and right mixers 1802 (1802L and 1802R) of the respective left and right channels each receive, in addition to the residual signals from the associated left or right earpiece microphone 27, 28 and the associated pass through signal from comms equalizer 1800, a signal indicative of the very low frequency components of the ambient noise used for controlling the system's susceptibility to very low frequency overloading. The very low frequency component of the ambient noise is suitably derived by low pas filter 1804R, 1804L operating upon the residual signal generated by the opposite channel, e.g. the output of the opposite channel mixer 1802. Each channel suitably includes two amplifiers; a first amplifier suitable for amplifying and filtering the residual signal, and a second amplifier suitable for mixing the residual signal with the audio pass through signal and the low frequency components of the residual signal of the opposite channel.

Referring again to FIG. 18, mixers 1802 suitably filter, amplify, and mix these signals. The outputs of mixers 1802 are provided to associated equalizers 1808. Equalizer 1808 suitably amplifies and attenuates specific frequencies of mixer 1802 signal to implement a transfer function representative of the electromechanical characteristics of the feedback system. Referring to FIG. 20, a suitable circuit for implementing equalizer 1808 includes four stages, each stage amplifying signals within a particular range of frequencies (e.g., centered upon 20 kHz, 1 kHz, 4 kHz and 100 kHz, respectively, preferably with high Q and narrow bandwidth) to compensate for the electromechanical properties of the cancellation system. Equalizer 1808 is suitably implemented as a Friend biquad circuit. A similar equalizer circuit may be used for each channel.

Once again with reference to FIG. 18, the output of each equalizer 1808 is a primary cancellation signal and establishes the bandwidth of the channel by filtering signals outside the bandwidth to maintain stability. The primary cancellation signal is provided to a muting circuit 1810 (1810R, 1810L), which may mute the cancellation signal according to signals received from an automatic gain control system. Muting circuit 1810 is activated when error amplifier 1816 indicates that headset 100 has been removed from the user's head. When muting circuit 1810 is activated, the primary cancellation signal from equalizer 1808 is cut off from power amplifier 1806. Because power amplifier 1806 does not receive the cancellation signal, power amplifier 1806 does not drive sound generator 22, reducing the current consumption of sound generator 22, thus conserving power and hence battery life. The 10 Hz signal from oscillator 1812 and the pass through signal from comms equalizer 1800, however, continue to be provided to sound generator 22 through power amplifier 1806. By continuing to provide the 10 Hz signal through the cancellation system, the cancellation system may determine whether the headset has been returned to the wearer's head.

Referring now to FIG. 21, muting circuit 1810 suitably comprises a switching transistor 2210 having its collector connected to ground and its emitter connected to the primary cancellation signal. The base of transistor 2210 is connected to the control signal generated by the automatic gain control system. When the control signal exceeds the conduction voltage of a diode 2212, the high signal is provided to the base, switching transistor 2210 on and connecting the primary cancellation signal to ground. Thus, if muting circuit 1810 is turned on, the primary cancellation signal is grounded and muting circuit 1810 has no output. If muting circuit 1810 is off, however, equalizer 1808 signal is provided to power amplifier 1806. A similar muting circuit controlled by the same control signal may suitably be provided for the other channel.

Returning to FIG. 18, power amplifier 1806 receives, in addition to the primary cancellation signal and the pass through input signal received from comms equalizer 1800, a 10 Hz signal from oscillator 1812 analogous to that described in conjunction with FIG. 10. The 10 Hz signal is effectively mixed with the cancellation and pass through input signals, amplified, and provided to sound generator 22.

In accordance with one aspect of the present invention, it has been determined that operation of these features is optimized by use of a stable 10 Hz signal. A suitable circuit for generating a 10 Hz signal having sufficiently stable amplitude is shown in FIG. 22. Oscillator 1812 includes two diodes 2410 and 2412 and three op amp circuit stages 2416, 2418 and 2420 to form a high-Q, non-inverting oscillator. Diodes 2410 and 2412 form a diode clipper that generates a 10 Hz signal, which is provided to a 10 Hz bandpass filter constituted by op amp stages 2416, 2418 and 2420 to eliminate distortion induced by the diode clipper. This circuit generates a particularly stable 10 Hz signal. The output of 10 Hz oscillator may be applied to both earpiece circuits. The 10 Hz signal is detected by microphone 28 and analyzed, as described in greater detail below, to determine whether an abnormal pressure is being applied to the earpiece or whether the headset has been taken off by the user.

Referring to FIG. 23, an exemplary power amplifier circuit 1806 suitably comprises a single bridge amplifier, such as a Motorola MC34119 amplifier. The 10 Hz signal from oscillator 1812 is suitably selectively provided to the amplifier in two ways. A switch 1900 is provided to selectively effect direct application of the 10 Hz signal to sound generator 22. The 10 Hz signal is mixed directly with the amplified signal and provided to sound generator 22. Thus, the 10 Hz signal is not affected by power amplifier's 1806 feedback system and the effects of voltage control attenuator 1814. The 10 Hz signal then maintains a stable amplitude. Consequently, only variation of parameters outside controller 6, e.g. pressure on the earpiece, alters the 10 Hz signal.

Alternatively, switch 1900 effects mixing of the 10 Hz signal with the audio input signal and the primary cancellation signal prior to amplification. The 10 Hz signal is, in this case, subject to variations in amplitude caused by voltage control attenuator 1814. This feature compensates for variations in the sensitivities of the microphone and controller, which may occur, for example, when a controller is compatible with several different headsets, each having different acoustic characteristics. Regardless of the particular sensitivities of the microphone and controller, this feature maintains the amplitude of the 10 HZ signal at the same level to permit proper sensing of pressure on earpiece 1.

Automatic gain control is effected by monitoring the 10 Hz signal through the internal microphones for variations indicating pressure changes exerted on the earpieces. More specifically, as shown in FIG. 18 the output of mixers 1802 of each channel, each including the detected 10 Hz signal, is applied from the associated earpiece to low pass or bandpass filter 1815 and error amplifier 1816. A suitable circuit for implementing error amplifier 1816 is shown in FIG. 24. Filter 1815 generates a signal representative of the 10 Hz component of the signal detected in the respective earpiece as it is affected by the properties of the earpiece, including changes caused by pressure on the earpiece. The 10 Hz signal is then provided to error amplifier 1816, suitably a differential amplifier, which generates an error signal corresponding to the sound pressure level of the 10 Hz signal as detected by microphone 28. Changes in the sound pressure level of the 10 Hz signal indicates abnormal pressure on earpiece 1 or removal of headset 100 from the user's head, and the error amplifier 1816 generates an error signal corresponding to the detected changes in the signal.

Error amplifier 1816 provides an output signal to muting circuit 1810. If the pressure on headset 100 is below a predetermined threshold, e.g. the headset has been removed, the error signal provided to muting circuit 1810 activates muting circuit 1810 and interrupts the primary cancellation signal to power amplifier 1806, thus disabling the noise cancellation system. Because the cancellation signal is muted, power amplifier 1806 does not drive sound generator 22, conserving power and battery life. In addition, the squeal or drone caused by instability is eliminated without turning off the entire headset system.

The error signal is also provided through level shifter 1818 to the respective voltage controllers 1814 (1814R, 1814L) to vary the gain of power amplifier s 1806 (1806R, 1806L) to maintain stability. A suitable circuit for implementing level shifter 1818 is shown in FIG. 25. Level shifter 1818 is included in the present system to provide a compatible bias voltage for power amplifiers 1806. Most of the components in the disclosed embodiment are biased around a reference voltage of zero. The power amplifier, however, is, in the preferred embodiment, biased around a reference voltage of ½ $V_{cc}$. Thus, level shifter 1818 provides the proper reference voltage for components biased around a different reference voltage than the other components.

Level shifter 1818 transmits the error signal to voltage controllers 1814, each of which is connected to the associated channel power amplifier 1806. Each voltage controller 1814 generates a suitable control signal responsive to the signal generated by error amplifier 1816 which is provided to the associated power amplifier 1806 to reduce power amplifier's 1806 gain when abnormal pressure is sensed on earpiece 1. A diagram of a suitable circuit for implementing voltage controller 1814 is shown in FIG. 26. Voltage controller 1814 includes a FET 2600 connected with gate receptive of the output of level shifter 1818, source connected to the output of a buffer (not shown) which converts power amplifier's 1806 reference voltage to low impedance from high impedance and filters noise generated by the supply, and drain connected to the feedback loop of power amplifier 1806, which controls the gain of power amplifier 1806. As the signal from error amplifier 1816 indicates increasing pressure on earpiece 1, the voltage applied to the gate FET 2600 changes, reducing the conductivity of FET 2600 and thus reducing the gain of power amplifier 1806. Thus, the gain of power amplifier 1806 is reduced when abnormal pressure is sensed on earpiece 1, and stability is maintained.

Although several different features are included in controller 6, many of these features are independent and may be included without the others, or in various combination. Circuit diagrams for several of these features are disclosed for illustrative purposes, though the features may be implemented using a variety of techniques known to those skilled in the art.

It is understood that while various of the conductors and connections are shown in the drawing as single lines, they are not shown in a limiting sense, and may comprise plural conductors or connections as understood in the art. Similarly, power connections, various control lines and the like, to the various elements are omitted from the drawing for the sake of clarity. Further, the above description is of preferred exemplary embodiments of the present invention, and the invention is not limited to the specific forms shown. Modifications may be made in the design and arrangements of the elements within the scope of the invention, as expressed in the claims.

What is claimed is:

1. An active noise canceling system comprising:

a sound generator, responsive to drive signals applied thereto, for generating an anti-noise field;

a noise cancellation processor, for generating the drive signals to the sound generator;

a first sound sensor disposed within said anti-noise field to generate a residual signal indicative of the sum of ambient sounds and anti-noise impinging on the sensor, wherein said noise cancellation processor processes the residual signal to form a component of the anti-noise field; and means for generating indicia of the level of ambient noise and responsively varying a transfer function of the system in response to said indicia of amplitude of ambient noise such that a gain of the transfer function of the system is decreased in response to a decrease in said indicia of amplitude of ambient noise, wherein the transfer function comprises a ratio of an output signal of the noise cancellation processor to at least the residual signal.

2. A method for increasing the stability of an active noise cancelling system comprising a noise cancellation circuit, a sound sensor and sound generator cooperating in a feedback loop, the feedback loop having an associated transfer function, the method including the steps of:

generating, in accordance with drive signals, an anti-noise field;

sensing the residual noise resulting from interaction of the anti-noise and ambient noise;

generating the drive signals in accordance with said sensed residual noise;

sensing ambient noise outside of the anti-noise field; and feeding forward a first range of frequencies that includes at least the high frequency components of the ambient noise to effect feedforward cancellation thereof;

wherein a feedback signal, generated by the feedback loop that processes a second range of frequencies, is processed by a noise cancellation processor without affecting the transfer function of the noise cancellation processor to form a component of said anti-noise field with the transfer function comprising a ratio of an output signal of the noise cancellation processor to at least said sensed residual noise, and wherein the first range of frequencies and the second range frequencies substantially overlap in a cancellation band below an enhancement frequency range.

3. An active noise canceling system, comprising:

a sound generator for generating an anti-noise field in response to drive signals applied thereto;

a first sound sensor, disposed within an anti-noise field, for generating a residual signal indicative of the sum of ambient noise and anti-noise impinging on the sensor;

a second sound sensor disposed a predetermined distance from said sound generator and output of said anti-noise field to generate a signal indicative of ambient noise; and a processor, for generating the drive signals to the sound generator in accordance with said residual signal and said signal indicative of said ambient noise;

wherein said first sound sensor is connected to cooperate with said processor and said sound generator to form a feedback loop that processes a first range of frequencies to produce a feedback signal, and said second sound sensor is connected to cooperate with said processor and said sound generator to provide feedforward signal noise cancellation of a second range of frequencies, said feedforward and feedback signals being processed by said processor to form a component of said anti-noise field, and wherein the first range of frequencies and the second range of frequencies substantially overlap in a cancellation band below an enhancement frequency range.

* * * * *